US011284899B2

(12) United States Patent
Ibrahim et al.

(10) Patent No.: US 11,284,899 B2
(45) Date of Patent: *Mar. 29, 2022

(54) LEFT ATRIAL APPENDAGE TREATMENT SYSTEMS AND METHODS

(71) Applicant: AtriCure, Inc., Mason, OH (US)

(72) Inventors: Tamer Ibrahim, Danville, CA (US); Dwight P. Morejohn, Davis, CA (US)

(73) Assignee: AtriCure, Inc., Mason, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/173,929

(22) Filed: Oct. 29, 2018

(65) Prior Publication Data
US 2019/0117229 A1    Apr. 25, 2019

Related U.S. Application Data

(60) Continuation of application No. 14/593,961, filed on Jan. 9, 2015, now Pat. No. 10,143,475, which is a continuation of application No. 14/244,671, filed on Apr. 3, 2014, now Pat. No. 8,932,308, which is a division of application No. 13/524,891, filed on Jun. 15, 2012, now Pat. No. 8,715,302.

(60) Provisional application No. 61/498,399, filed on Jun. 17, 2011.

(51) Int. Cl.
A61B 17/12    (2006.01)
A61B 17/29    (2006.01)

(52) U.S. Cl.
CPC .. *A61B 17/12009* (2013.01); *A61B 17/12013* (2013.01); *A61B 2017/2923* (2013.01); *A61B 2017/2927* (2013.01)

(58) Field of Classification Search
CPC .... A61B 17/12013; A61B 2017/00243; A61B 17/0469; A61B 17/12009; A61B 17/32056; A61B 17/221; A61B 2017/00575; A61B 2017/0475; A61B 2017/2927
See application file for complete search history.

(56) References Cited

U.S. PATENT DOCUMENTS

| 10,143,475 B2 | 12/2018 | Ibrahim et al. |
| 2008/0312664 A1 | 12/2008 | Bardsley et al. |
| 2010/0069925 A1 | 3/2010 | Friedman et al. |

*Primary Examiner* — Katherine M Shi
(74) *Attorney, Agent, or Firm* — Levine Bagade Han LLP

(57) ABSTRACT

Embodiments of the present invention encompass systems and methods to prevent complications from atrial fibrillation by preventing or reducing the likelihood of blood flow out of the left atrial appendage, to eliminate a possible source of aberrant electrical circuits, or both. Accordingly, techniques are provided for delivering ligature loops or closure means to the left atrial appendage, and to other anatomical structures of a patient which may be desirable in other surgical procedures.

20 Claims, 33 Drawing Sheets

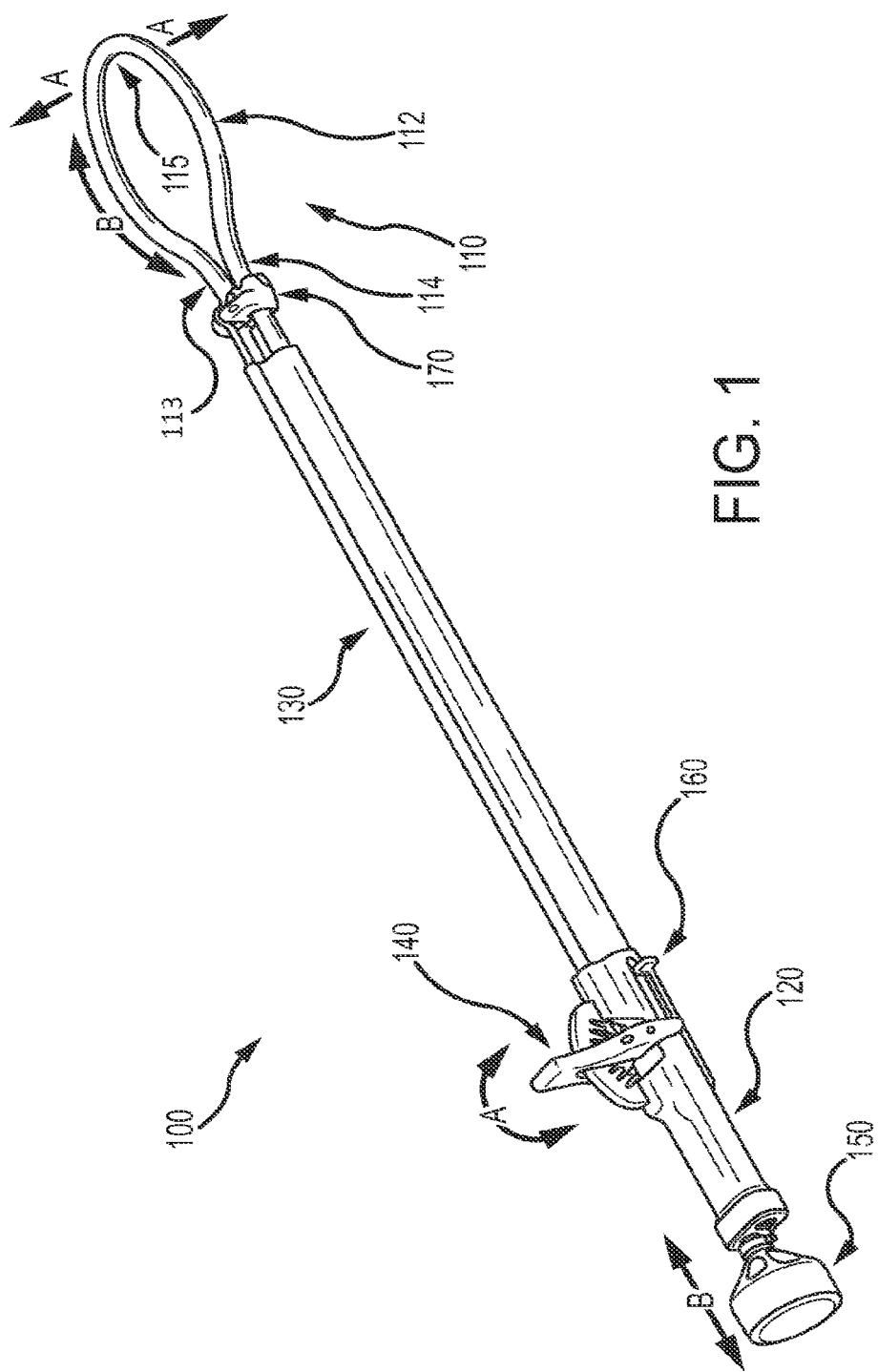

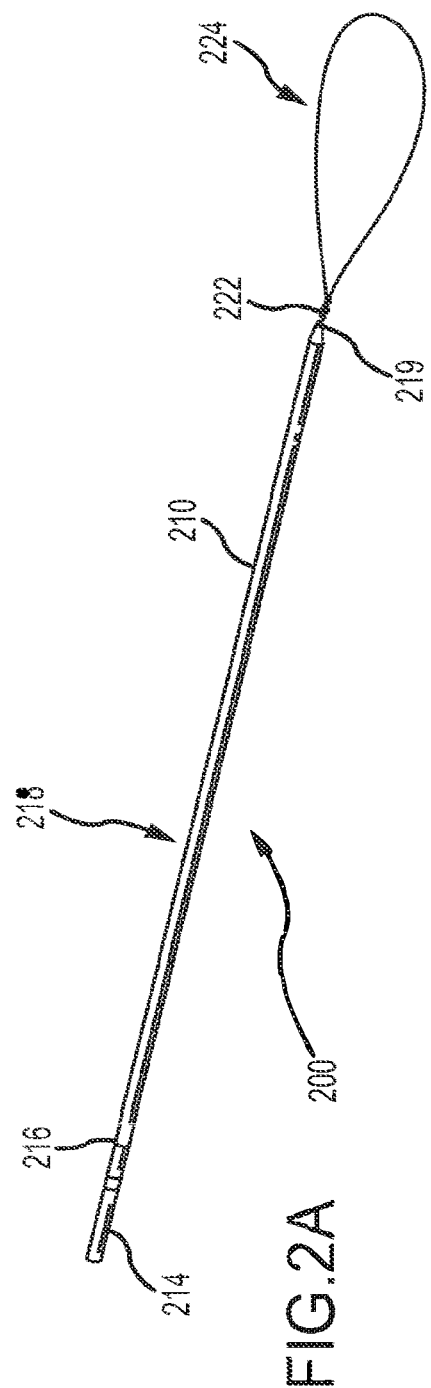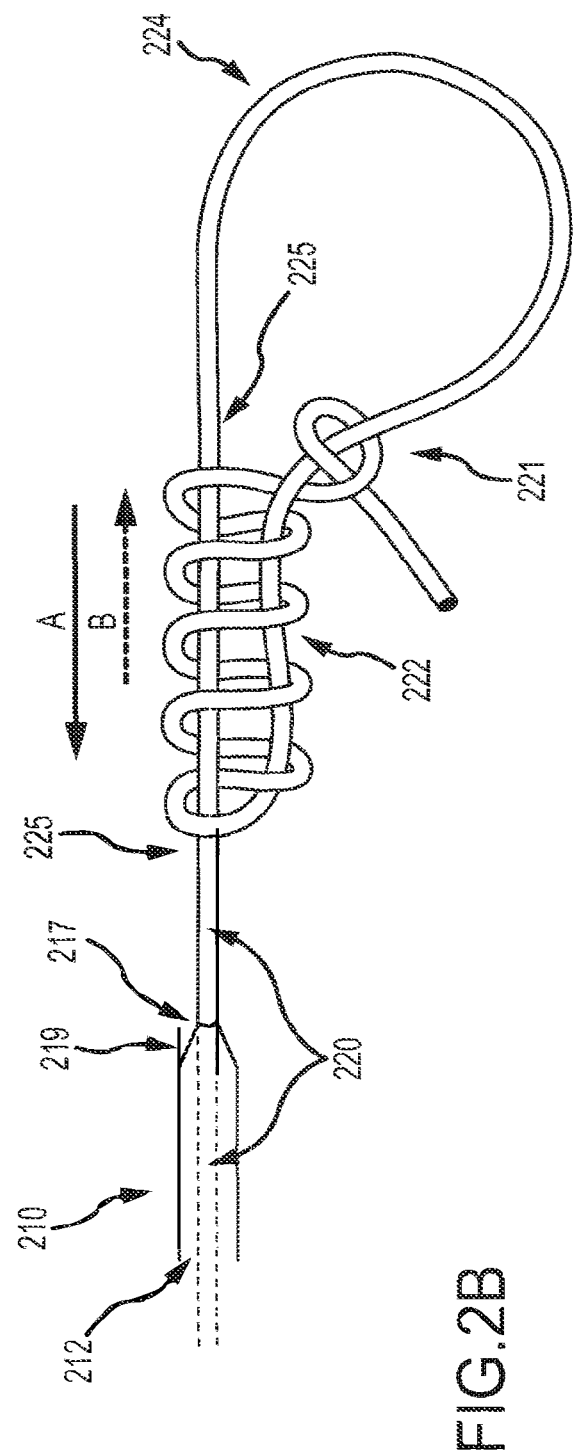

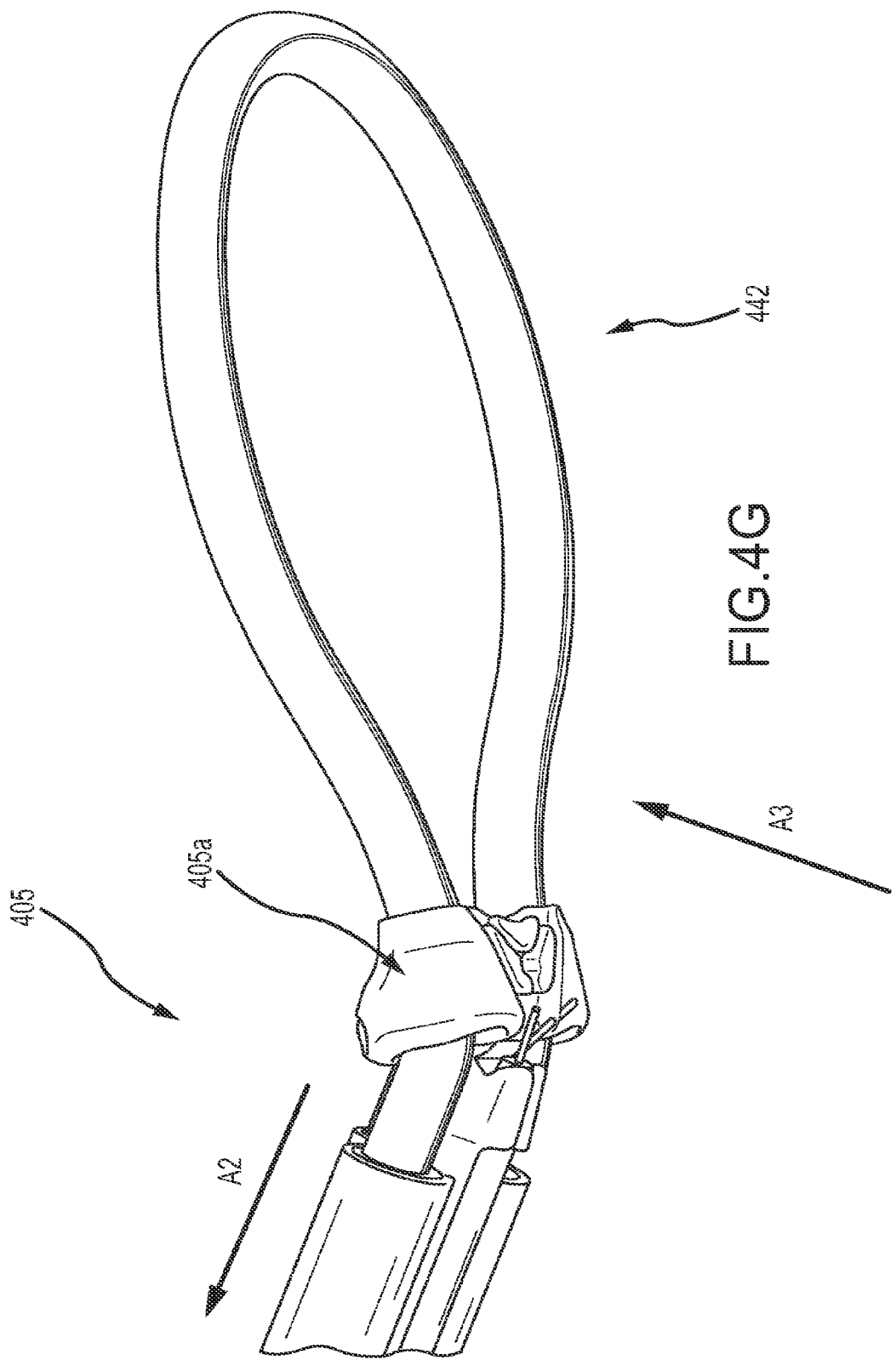

LEFT ATRIAL APPENDAGE TREATMENT SYSTEMS AND METHODS

CROSS-REFERENCE TO RELATED APPLICATIONS

This application continuation U.S. patent application Ser. No. 14/593,961 filed Jan. 9, 2015, which is a continuation of U.S. patent application Ser. No. 14/244,671 filed Apr. 3, 2014, which is a divisional of U.S. patent application Ser. No. 13/524,891 filed Jun. 15, 2012, which claims the benefit of U.S. Provisional Patent Application No. 61/498,399 filed Jun. 17, 2011, the content of which are incorporated herein by reference in their entirety.

BACKGROUND OF THE INVENTION

Embodiments of the present invention relate to systems and methods for closing anatomical structures of a patient. Particular embodiments related to techniques for closing the left atrial appendage of a patient.

Atrial fibrillation (AF) is a heartbeat rhythm disorder (or "cardiac arrhythmia") in which the upper chambers of the heart known as the atria quiver rapidly instead of beating in a steady rhythm. This rapid quivering reduces the heart's ability to properly function as a pump. AF is characterized by circular waves of electrical impulses that travel across the atria in a continuous cycle. It is the most common clinical heart arrhythmia, affecting more than two million people in the United States and some six million people worldwide.

Atrial fibrillation typically increases the risk of acquiring a number of potentially deadly complications, including thrombo-embolic stroke, dilated cardiomyopathy and congestive heart failure. Quality of life is also impaired by common AF symptoms such as palpitations, chest pain, dyspnea, fatigue and dizziness. People with AF have, on average, a five-fold increase in morbidity and a two-fold increase in mortality compared to people with normal sinus rhythm. One of every six strokes in the U.S. (some 120,000 per year) occurs in patients with AF, and the condition is responsible for one-third of all hospitalizations related to cardiac rhythm disturbances (over 360,000 per year), resulting in billions of dollars in annual healthcare expenditures.

AF is the most common arrhythmia seen by physicians, and the prevalence of AF is growing rapidly as the population ages. As the prevalence of AF increases, so will the number of people who develop debilitating or life-threatening complications, such as stroke. According to Framingham Heart Study data, the stroke rate in AF patients increases from about 3% of those aged 50-59 to more than 7% of those aged 80 and over. AF is responsible up to 35% of the strokes that occur in people older than age 85.

Efforts to prevent stroke in AF patients have so far focused primarily on the use of anticoagulant and antiplatelet drugs, such as warfarin and aspirin. Long-term warfarin therapy is recommended for all AF patients with one or more stroke risk factors, including all patients over age 75. Studies have shown, however, that warfarin tends to be underprescribed for AF. Despite the fact that warfarin reduces stroke risk by 60% or more, only 40% of patients age 65-74 and 20% of patients over age 80 take the medication, and probably fewer than half are on the correct dosage. Patient compliance with warfarin is problematic, and the drug requires vigilant blood monitoring to reduce the risk of bleeding complications.

Electrophysiologists classify AF by the "three Ps": paroxysmal, persistent, or permanent. Paroxysmal AF—characterized by sporadic, usually self-limiting episodes lasting less than 48 hours—is the most amenable to treatment, while persistent or permanent AF is much more resistant to known therapies. Researchers now know that AF is a self-perpetuating disease and that abnormal atrial rhythms tend to initiate or trigger more abnormal rhythms. Thus, the more episodes a patient experiences and the longer the episodes last, the less chance of converting the heart to a persistent normal rhythm, regardless of the treatment method.

AF is characterized by circular waves of electrical impulses that travel across the atria in a continuous cycle, causing the upper chambers of the heart to quiver rapidly. At least six different locations in the atria have been identified where these waves can circulate, a finding that paved the way for maze-type ablation therapies. More recently, researchers have identified the pulmonary veins as perhaps the most common area where AF-triggering foci reside. Technologies designed to isolate the pulmonary veins or ablate specific pulmonary foci appear to be very promising and are the focus of much of the current research in catheter-based ablation techniques.

One possible complication as a result of AF is that clots from the left atrial appendage may embolize and cause harm to the patient. For example, dislodged clots can form emboli that lead to ischemic damage to a person's brain, kidneys, or other organs. Although left atrial appendage closure devices and techniques are currently available and provide real benefits to patients in need thereof, significant advances may still be made to provide improved systems and methods for treating the left atrial appendage. Embodiments of the present invention provide solutions and answers to at least some of these outstanding needs.

BRIEF SUMMARY OF THE INVENTION

Embodiments of the present invention encompass systems and methods for delivering closure means to an anatomical structure of a patient, such as a left atrial appendage. Exemplary systems may include a guiding mechanism, closure delivery means, or suture carrier that delivers or applies a closure means or occlusive device to the patient anatomy. In use, for example, a surgeon or operator may obtain or hold a ligature assembly, which includes a carrier tube and knotted suture loop, and separate a frangible portion of the carrier tube away from the main body of the tube shaft. This may be done by snapping the carrier tube along a break line which is scored on the tube. Often, a proximal tail of the knotted ligature thread is glued or crimped to, or otherwise attached with, the proximal frangible portion of the carrier tube. The user can place the suture thread loop about a cinchable loop of a delivery mechanism, and then use the cinchable loop so as to precisely and efficiently position the suture thread loop within the patient. Because the ligature assembly is engaged with the delivery mechanism, the two can be operated or manipulated as a single unit by a surgeon or other user. By actuating the delivery mechanism, the user can safely cinch the suture loop about the patient anatomy without causing harm or presenting undue risk to the patient. When a suture loop is positioned about the anatomical structure as desired, the operator can grasp or tug on an exposed proximal suture portion, and cut the suture thread, so as to decouple the cinched suture loop of the ligature assembly from the ligature delivery system. Hence, from the time the ligature assembly is loaded onto the ligature delivery system, until the time the ligature delivery system is retracted from the patient, the engagement between the ligature assembly and the ligature delivery system allows the physician or operator to use the combination as a single unit in a simple, efficient, and effective manner. In this way, the combination of the ligature snare with the ligature delivery system provides a significant improvement to existing snare technology. The delivery system can be withdrawn from the patient upon completion of the procedure and the applied suture loop or closure means then operates to ligate the anatomical structure.

In one aspect, embodiments of the present invention encompass ligature delivery systems for use with a left atrial appendage ligature assembly. Exemplary ligature delivery systems include a thread delivery mechanism having a cinchable loop that receives a thread of the ligature assembly and that rotates axially about a central longitudinal axis between a first configuration whereby the thread is shielded from a left atrial appendage of a patient and a second configuration whereby the thread can be released onto the left atrial appendage. Ligature delivery systems may also include a delivery control mechanism that cinches the cinchable loop about the left atrial appendage and that switches the cinchable loop between the first and second configurations. Ligature delivery systems may also include a support mechanism having a first engagement assembly that receives a carrier of the ligature assembly, and a second engagement assembly coupled with the delivery control mechanism. Ligature delivery systems may also include a deflector mechanism that pivots relative to the support mechanism and that is coupled with the loop. Ligature delivery systems may further include a deflection control mechanism having an actuation assembly and a linkage assembly. The linkage assembly can be coupled with the actuation assembly and the deflector mechanism, such that movement of the actuation assembly relative to the support mechanism causes the deflector body and loop to pivot relative to the support mechanism. In some instances, the cinchable loop includes a flexible cylinder having a longitudinally extending slot that receives the thread. In some instances, the cinchable loop includes a first section that translates longitudinally relative to a first guide of the deflector mechanism, and a second section that is translationally fixed relative to a second guide of the deflector mechanism. In some instances, the delivery control mechanism effects coordinated axial rotation between a first end portion of the delivery mechanism and a second end portion of the delivery mechanism, and the first and second end portions border or bound a central portion of the loop. In some instances, the delivery control mechanism includes a gearbox assembly in operative association with the first and second end portions. Operation of the gearbox can affect or cause the coordinated axial rotation. In some instances, the delivery control mechanism includes a first rotary drive coupled with a first section of the cinchable loop and a second rotary drive coupled with a second section of the cinchable loop, such that torque applied to either drive is transmitted between the first and second drives, and operates to rotate the cinchable loop. In some instances, the delivery control mechanism includes a first rotary drive coupled with a first section of the cinchable loop and a second rotary drive coupled with a second section of the cinchable loop, such that rotation of the first rotary drive drives counter-rotation of the second rotary drive, and the rotating drives coordinate to switch the cinchable loop from the first configuration to the second configuration. In some instances, the second engagement assembly includes a first lumen and a second lumen. In some cases the delivery control mechanism includes a first rotary drive disposed within the first lumen of the second engagement assembly. In some cases the first rotary drive is coupled with a first section of the cinchable loop. In some cases the delivery control mechanism includes a second rotary drive disposed within the second lumen of the second engagement assembly. In some cases the second rotary drive is coupled with a second section of the cinchable loop. The first rotary drive can be rotatable and translatable within the first lumen, and the second rotary drive can be rotatable within the second lumen. In some cases the second rotary drive can translate within the second lumen. In some cases the second rotary drive does not translate within the second lumen.

In another aspect, embodiments of the present invention encompass methods for delivering a ligature loop to a left atrial appendage of a patient. Exemplary methods may include placing a ligature loop of a ligature assembly about the left atrial appendage while the ligature loop is engaged with a cinchable loop of a ligature delivery system. Methods may also include rotating the cinchable loop from a first configuration, where the ligature loop is shielded from the left atrial appendage by the cinchable loop, to a second configuration, where the ligature loop can be deployed to the left atrial appendage. The rotation can be performed while the ligature loop and the cinchable loop encircle the left atrial appendage. Methods can also include deploying the ligature loop from the cinchable loop onto the left atrial appendage. In some instances, methods include cinching the cinchable loop about the left atrial appendage prior to rotating the cinchable loop to deploy the ligature loop. In some instances, the cinchable loop includes a groove, and the ligature loop is engaged with the groove when the cinchable loop is in the first configuration, and is deployed from the groove when the cinchable loop is in the second configuration. Hence, methods may involve engaging the ligature loop with the groove when the cinchable loop is in the first configuration, and deploying the ligature loop from the groove to the left atrial appendage when the cinchable loop is in the second configuration. In some instances, the ligature assembly includes a carrier tube, the ligature delivery system includes a support mechanism coupled with the cinchable loop, and the carrier tube is engaged with the support mechanism when the ligature loop is placed about the left atrial appendage. Hence, methods may include engaging a carrier tube of a ligature assembly with a support mechanism of the ligature delivery assembly. In some instances, the ligature assembly includes a knot or a ratchet mechanism. In some instances, a ligature assembly may be provided as a band or loop. In some instances, methods may include securing the left atrial appendage with a grasping mechanism prior to placing the ligature loop about the left atrial appendage. In some instances, methods may include advancing the ligature loop over the grasping mechanism prior to rotating the cinchable loop.

In still another aspect, embodiments of the present invention encompass ligature delivery systems which can be used with any of a variety of left atrial appendage closure mechanisms or other anatomical structure closure mechanisms or means. Exemplary ligature delivery systems include a delivery mechanism having a cinchable loop that engages the closure mechanism and that rotates axially about a central longitudinal axis between a first configuration, where the closure mechanism is shielded from an anatomical structure such as a left atrial appendage or cecal appendix of a patient, and a second configuration, where the closure mechanism can be released onto the anatomical structure. Systems may also include a delivery control mechanism that cinches the cinchable loop about the anatomical structure and that switches the cinchable loop between the first and second configurations. In some instances, the cinchable loop includes a groove that engages the closure mechanism when the cinchable loop is in the first configuration. In some instances, the delivery control mechanism includes a first rotary drive coupled with a first portion of the cinchable loop and a second rotary drive coupled with a second portion of the cinchable loop. In some instances, systems include a support mechanism having a recess that receives a proximal tail portion of the closure mechanism.

The terms "invention," "the invention," "this invention" and "the present invention" used in this patent are intended to refer broadly to all of the subject matter of this patent and the patent claims below. Statements containing these terms should be understood not to limit the subject matter described herein or to limit the meaning or scope of the patent claims below. Embodiments of the invention covered by this patent are defined by the claims below, not this Summary. This Summary is a high-level overview of various aspects of the invention and introduces some of the concepts that are further described in the Detailed Description section below. This Summary is not intended to identify key or essential features of the claimed subject matter, nor is it intended to be used in isolation to determine the scope of the claimed subject matter. The subject matter should be understood by reference to appropriate portions of the entire specification of this patent, any or all drawings and each claim.

The above described and many other features and attendant advantages of embodiments of the present invention will become apparent and further understood by reference to the following detailed description when considered in conjunction with the accompanying drawings.

BRIEF DESCRIPTION OF THE SEVERAL VIEWS OF THE DRAWINGS

FIG. 1 depicts aspects of ligature delivery systems and methods according to embodiments of the present invention.

FIGS. 2A, 2B, and 2C illustrate features of ligature assemblies according to embodiments of the present invention.

FIGS. 4A to 4G show features of ligature delivery systems and methods according to embodiments of the present invention.

FIGS. 12, 12A-1, 12A-2, and 12A-3 show aspects of ligature delivery systems and methods according to embodiments of the present invention.

DETAILED DESCRIPTION OF THE INVENTION

Figure 2C:
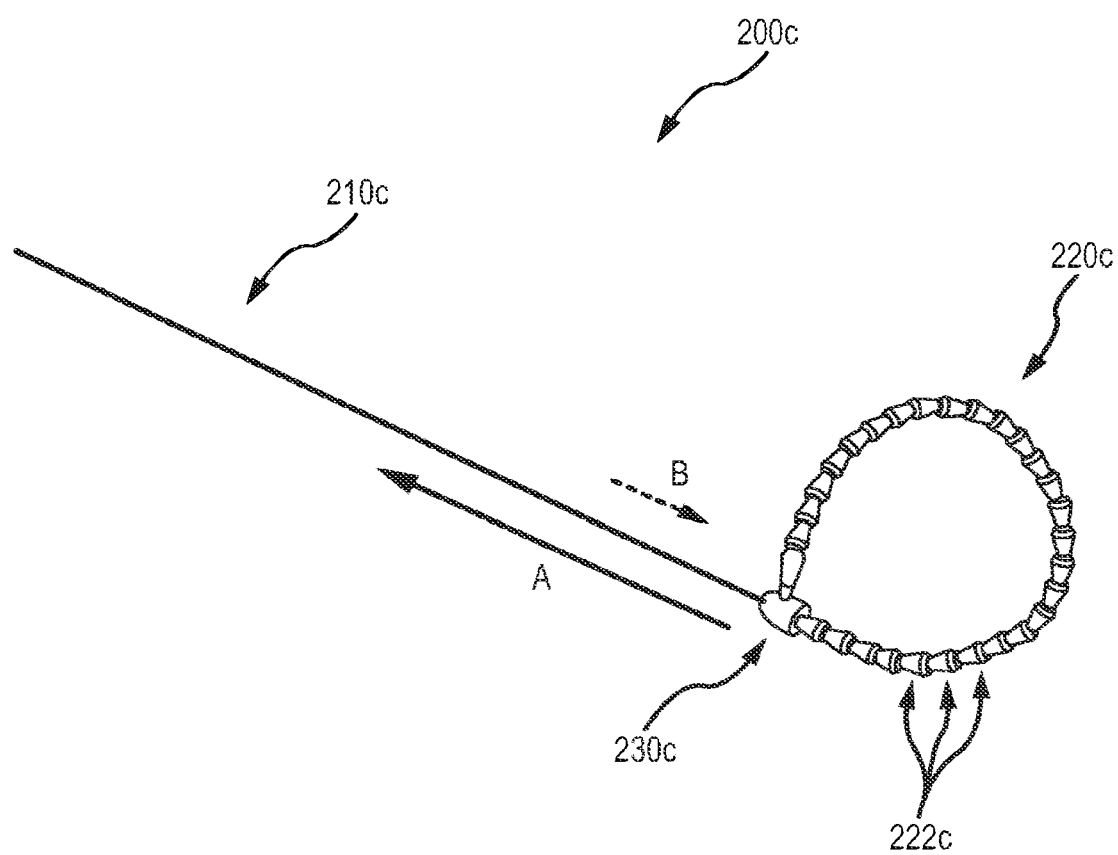

The subject matter of embodiments of the present invention is described here with specificity to meet statutory requirements, but this description is not necessarily intended to limit the scope of the claims. The claimed subject matter may be embodied in other ways, may include different elements or steps, and may be used in conjunction with other existing or future technologies. This description should not be interpreted as implying any particular order or arrangement among or between various steps or elements except when the order of individual steps or arrangement of elements is explicitly described.

Embodiments of the present devices provide delivery systems and methods for applying ligatures or sutures to anatomical features of a patient. In some cases, delivery systems and methods can be used with pre-fabricated ligature assembly or pre-knotted suture thread loop. For example, a ligature assembly or snare apparatus may include a suture or thread that is tied with a one-way knot or hangman's noose, or that is otherwise configured with a one-way control mechanism such as a ratchet. The ligature assembly may include an elongate proximal tail, optionally disposed within a carrier such as a stiff cylindrical tube. In some instances, the proximal tail portion may be glued or otherwise affixed to a proximal portion of the carrier tube. Relatedly, the proximal portion of the carrier tube may have a score mark or other means by which the carrier tube can be easily or neatly broken apart, so as to provide a proximal frangible portion and a more distal main body tube. In some instances, the score mark or breakable feature may be located approximately one to two inches from the proximal end of the tube or carrier. In use, the operator or surgeon may break off the proximal frangible portion, and proximally retract or pull the frangible portion relative to the main body tube. The knot or ratchet mechanism may be held by a distal portion of the main body tube, such that as the operator draws the proximal tail thread portion away from the main body tube, the knot or ratchet remains snug against the distal carrier tube portion as a looped portion of the thread distal to the knot becomes cinched. In this way, the surgeon or user can apply opposing forces to the thread knot and the proximal thread tail, so as to tighten the thread loop about an anatomical feature such as the left atrial appendage. Typically, the ligature assembly is provided as a single-use device.

Ligature delivery device systems and methods disclosed herein can be used with such ligature assemblies so as to provide an efficient and effective approach for delivering looped suture thread to anatomical features of the patient. Such techniques allow the user or surgeon to easily maneuver the distal thread loop about the patient's anatomy, and to control the placement of the distal thread loop as desired. What is more, the present systems and methods may allow the surgeon or operator to firmly cinch the thread loop about the patient's anatomy, without cutting into the patient's tissue. Hence, for example, the present techniques are well suited for use in a minimally invasive approach.

Embodiments of the present invention provide systems and methods for performing epicardial closure of the left atrial appendage. Such systems and methods can be used through any desired surgical access modality, including without limitation sternotomy, thoracotomy, and other procedures as discussed elsewhere herein.

Exemplary systems may include a grasping means or suction member that can be used to adhere to tissue and extend the appendage, so that a closure means or occlusive device can be delivered to the appendage base. Exemplary embodiments provide mechanically simple, user friendly devices, which can be used to apply any of a variety of ligature assemblies or closure means to patient tissue, which are easy to load and reload with such ligature assemblies, and which can be used to efficiently deliver a ligature suture to the tissue (e.g. base of left atrial appendage) while as the same time protecting the tissue from potential cutting effects that may otherwise occur when tightening a ligature thread about the tissue.

Figure 12:
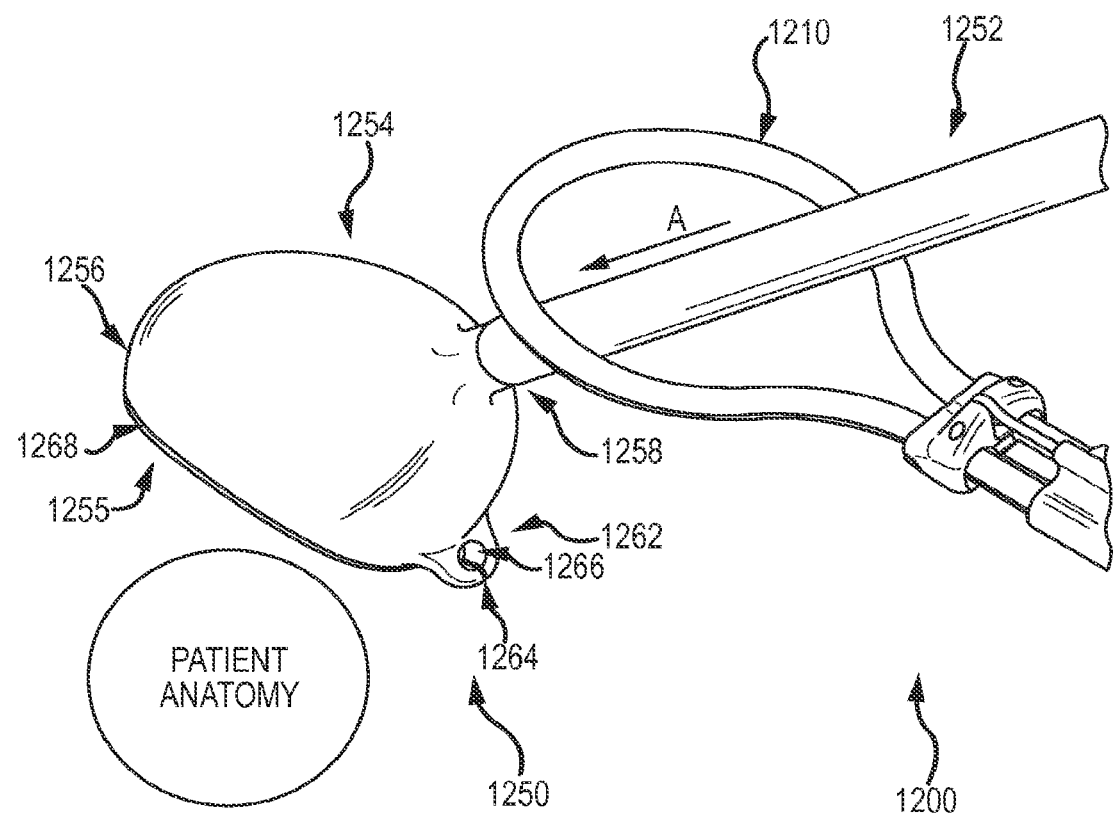
Figures 1, 12A:
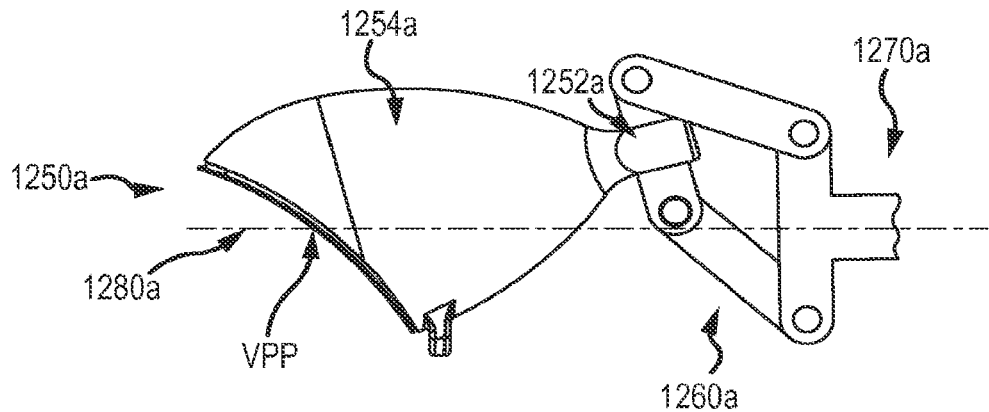
Figures 2, 12A:
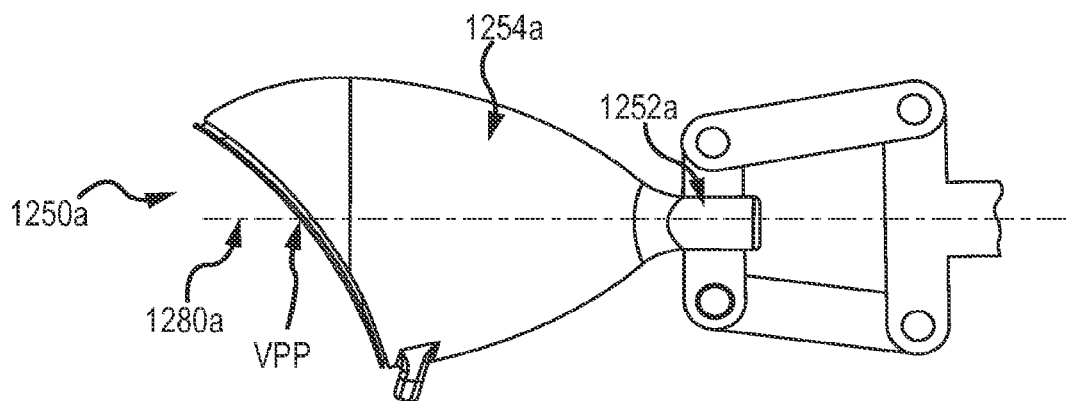
Figures 3, 12A:
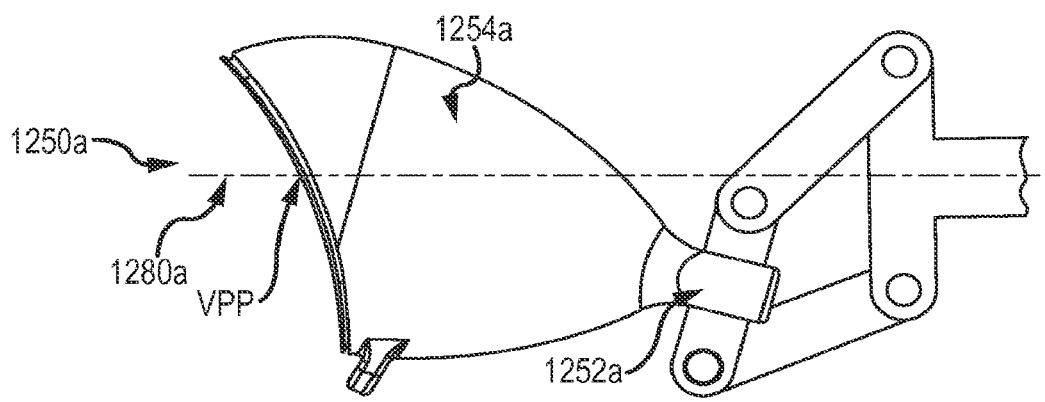

Turning now to the drawings, FIG. 1 illustrates aspects of an exemplary ligature delivery system 100 according to embodiments of the present invention. As shown here, the delivery system 100 includes a suture carrier, guiding mechanism, or thread delivery mechanism 110 disposed toward a distal portion of the system, and a handle mechanism 120 disposed toward a proximal portion of the system. Delivery system 100 also includes a main body or support mechanism 130, a deflection control mechanism 140, a deflector mechanism 170, and a delivery control mechanism 150 which may include a knob assembly. In some instances, the handle mechanism may be integral to and part of the support mechanism 130. As further described herein, a surgeon or operator can use delivery system 100 to administer or deliver a ligature thread or closing means to an anatomical feature of a patient. For example, the delivery system can be loaded with a ligature assembly (see e.g. FIGS. 2A and 2B), such that a ligature thread loop of the ligature assembly is disposed about or received by a loop portion or cinchable loop 112 of the thread delivery mechanism 110, and a knot pusher tube of the ligature assembly is coupled with or received by the with the support mechanism or main body 130. The operator can then maneuver the ligature thread loop, by using the deflection control mechanism 140 to deflect the suture carrier loop portion 112, as indicated by the A arrows. The operator can also expand and contract the ligature thread loop, by using the delivery control mechanism 150 to extend and retract one side of the suture carrier loop portion 112 (to which the thread loop is engaged), as indicated by the B arrows. As discussed elsewhere herein, once the ligature thread is positioned as desired, the operator can then deploy the ligature thread to the intended anatomical target by actuating the delivery control mechanism 150, which in turn rotates the suture carrier or thread delivery mechanism 110. In this way, the suture carrier 110 can operate as a guiding mechanism or delivery means for the ligature thread. In some instances, the delivery system may also include an ejector mechanism having an ejector handle 160. In some instances, a ligature delivery system may be provided as a disposable single-patient use product, such that the system may be used to apply several ligatures or sutures to an individual patient during the course of a surgical procedure, and thereafter discarded. In some instances, the applicator mechanism can be triggered outside of the patient. Activation of the delivery mechanism may act to cinch a lasso or compress a self-locking clip, for example.

Ligature Assemblies

FIGS. 2A and 2B illustrate aspects of an exemplary ligature assembly 200 according to embodiments of the present invention. In some cases, a ligature assembly may be referred to as a ligating loop or a surgical snare. As depicted here, the ligature assembly 200 includes an elongate tubular shaft or knot pusher 210 having a lumen 212 therein, and a ligature thread or closure means or mechanism 220 disposed at least partially within the lumen of the tubular shaft or carrier 210. In some instances, a ligature assembly can be provided as a left atrial appendage ligature assembly. The ligature thread 220 can be pre-formed or pre-tied in such a way so as to present a knot 222 and a loop portion 224. Generally, the knot 222 is disposed toward a distal portion 221 of the thread 220, and a proximal portion of the thread extends within the shaft lumen 212. In some instances, the tubular shaft may include a detachable or frangible proximal portion 214, and a proximal portion of the thread is attached with the detachable portion 214. For example, the proximal portion of the thread may be glued to the detachable portion 214. As shown here, the tubular shaft 210 may include a score line 216, and the tubular shaft can be broken along the score line 216 so as to separate the frangible portion 214 from a central portion or main body 218 of the shaft 210. For example, the surgeon or operator may bend the push tube 10 so that the frangible portion 214 cracks off, away from the main body 218. Once severed, the frangible portion 214 can be used to pull the proximal thread tail out of the carrier tube, via a proximal end of the main body 218, thus tightening or cinching the ligature loop 224. Typically, the thread or occlusive device 220 extends distally out of the shaft 210, for example through an aperture 217 of a tapered distal portion 219 of the shaft.

According to some embodiments, the knot 222 is provided as a slip knot, sliding knot, running knot, or the like. For example, as the user or operator pulls the frangible portion 214, and as the distal portion of the main body 218 holds the knot 222 in place, the knot 222 can allow a portion 225 of the thread sliding therethrough to move lengthwise freely in one direction of pull (e.g. proximally toward the tube) as indicated by arrow A, while preventing or inhibiting the portion 225 from sliding lengthwise in the opposite direction of pull indicated by arrow B. In this way, the knot 222 can perform as a non-return knot. A knot 222 may be provided as a simple knot or a complex knot. Suitable knot configurations may also include laparoscopic knots, endoscopic knots, intracorporal knots, extracorporal knots, intraabdominal knots, surgical knots, and the like. In some instances, a ligature assembly may include a knotted thread or suture having a distal loop portion and a proximal tail portion, without a carrier or push tube. As further discussed elsewhere herein, the ligature delivery systems and methods provided in the instant disclosure allow a surgeon or operator to constrict the loop 224 about the patient's anatomy without having the sliding portion 225 cut into or form a groove in the patient's tissue.

FIG. 2C illustrates another exemplary ligature assembly or snare 200c according to embodiments of the present invention. As shown here, the ligature assembly includes a proximal tail portion 210c and a distal portion 220c which can be formed into a loop, for example by passing the proximal portion through a ratchet mechanism 230c. In this way, the distal portion can provide a ligature loop or closure means. The distal portion includes a series of projections 222c which may include teeth, barbs, beads, or the like. Typically, the projections are shaped so that they can be easily pulled through the ratchet mechanism 230c in one direction as indicated by arrow A, and resist movement through the ratchet mechanism 230c in the opposing direction as indicated by arrow B. For example, the projection may be triangular in shape or have a sloped surface. In this way, the coordinated operation between the projections 222c and the ratchet mechanism 230c operate in a manner similar to that of a one-way or non-return knot. In some instances, the ratchet mechanism 230c may include a flexible pawl deforms when rigid projections are passed along the ratchet. In some cases, the projections are flexible and deform when passed along a rigid pawl of the ratchet. Once the projection proceeds past the ratchet or pawl (in the direction indicated by arrow A), it is prevented or inhibited from returning in the opposite manner (as indicated by arrow B). In this way, the loop or closure mechanism can be cinched or constricted as desired to a particular diameter or size, and when the projection is locked against the ratchet or pawl the loop cannot be expanded or uncinched.

In some cases, a ligature assembly includes a threadlike suture that can reside partially within a tube or carrier. In some case, the suture is pre-formed with a knot. Hence, when a looped distal end of the ligature is positioned at a desired location about the LAA, the proximal portion of the ligature can be pulled or actuated, so as to tighten the loop, thus securing the knot. Some ligature assemblies may include a suture which extends from a distal end of the carrier in the form of a loop, having a sliding knot which secures itself when tightened. In some cases, ligature assemblies include a suture that is non-absorbable by the patient's body. Embodiments of the present invention encompass systems and methods for use in conjunction with such ligature assemblies, for the delivery of a suture to the patient's LAA.

Commercially available ligature assemblies include Surgitie™ single use ligating loops and ENDOLOOP® ligatures. Often, such pre-fabricated or pre-tied ligature assemblies are packaged so that proximal tail portion of the ligature thread is disposed within the carrier tube shaft, and the knot and loop portions extend distally from or beyond the carrier tube or pushrod. A proximal portion of the tube or pushrod can be snapped off, exposing the proximal tail of the ligature thread. Exemplary knots and ligature assemblies are described in European patent number EP 0477020 and German patent number DE 566173, and by Hage, Surg. Laparosc. Endosc. Percutan. Tech., February 18(1):1-7 (2008), the contents of which are incorporated herein.

Exemplary ligature assemblies often include a tube or carrier, and a ligature thread. In some cases, the tube or carrier can be fabricated of nylon or another suitable material. The thread or suture can include plain gut elements, synthetic polymers or copolymers, polymeric filaments, monofilament, polyester or other suitable materials, coated configurations, braided configurations or threads, and the like. In some instances, the diameter of the ligature thread may be between about 15 and 20 thousandths of an inch. In some instances, other thread diameters may be used. It is understood that the ligature delivery system may include thread guides, slots, grooves, and the like, which are sized or configured to operate with any ligature thread diameter, cross-section, or configuration. Similarly, the ligature delivery system may include knot or ratchet guides, pockets, stops, and the like, which are sized or configured to operate with any ligature thread knot or ratchet size or configuration.

In some instances, an exemplary system may include a closure delivery means that presents a semi-rigid profile which provides an elongate clamping surface. In some instances, the closure delivery means may also include or operate in coordination with a hypotube assembly that houses or receives portions of a closure means, such as a ligature. The closure means may be in the form of a loop, a snare, a lasso, a noose, or the like. The closure means may also include a ligature or tie having a knot such as a one-way knot or slip knot. The system may also include a tension force limiter that decouples the shaft from the ligature at a preset load, for example by using a spring.

In some embodiment, the ligature assembly or closure means may include an elastic or stretchable band or ligature loop that does not include a knot, ratchet, or proximal tail. Such a closure means or mechanism can be wrapped in a generally circumferential manner about the cinchable loop of the ligature delivery system. In some cases, the band or loop may be disposed at least partially in a groove or recess of the cinchable loop, or the band or loop may be engaged with a guide of the cinchable loop or be otherwise engaged with the cinchable loop, such that the band or loop resides upon the cinchable loop with the cinchable loop is in a first configuration (see e.g. FIG. 8A), and the band or loop is deployed or released from the cinchable loop to the target tissue when the cinchable loop is in a second configuration (see e.g. FIG. 8D). The cinchable loop can be converted from the first configuration to the second configuration by, for example, rotating the cinchable tube loop about a central longitudinal axis of the loop tube. In some cases, such a band or loop may have a cross-section diameter within a range from about 0.10 inch to about 0.25 inch. In such cases, the delivered band or loop is not held in place upon the target anatomy due to a one way knot or ratchet mechanism, but rather is held in place by the elasticity of the band or loop itself. In some cases, such a band or loop can be delivered to a target anatomy over a suction device or grasping means (see e.g. FIG. 12).

In some instances, a surgical tie total loop circumference beyond the snare tip can be about 9.3 inches. A loop circumference at the base of an LAA can be about 4 inches. In many patients, the base of the LAA may be about 5 inches in circumference. In some instances, the excess double length can be about 5 inches total. Such an excess of ligature length may be difficult to manage if loose. In some situations, a surgeon or operator may pull in about 2 to 3 inches before mounting in the snare. A slack puller on a finger opposite the snare arm can allow a single pull handle at the back to cinch up the snare and the snare tip could reside in a nose scoop. The surgeon or operator may load the slack-pulling finger as well.

Figure 3:
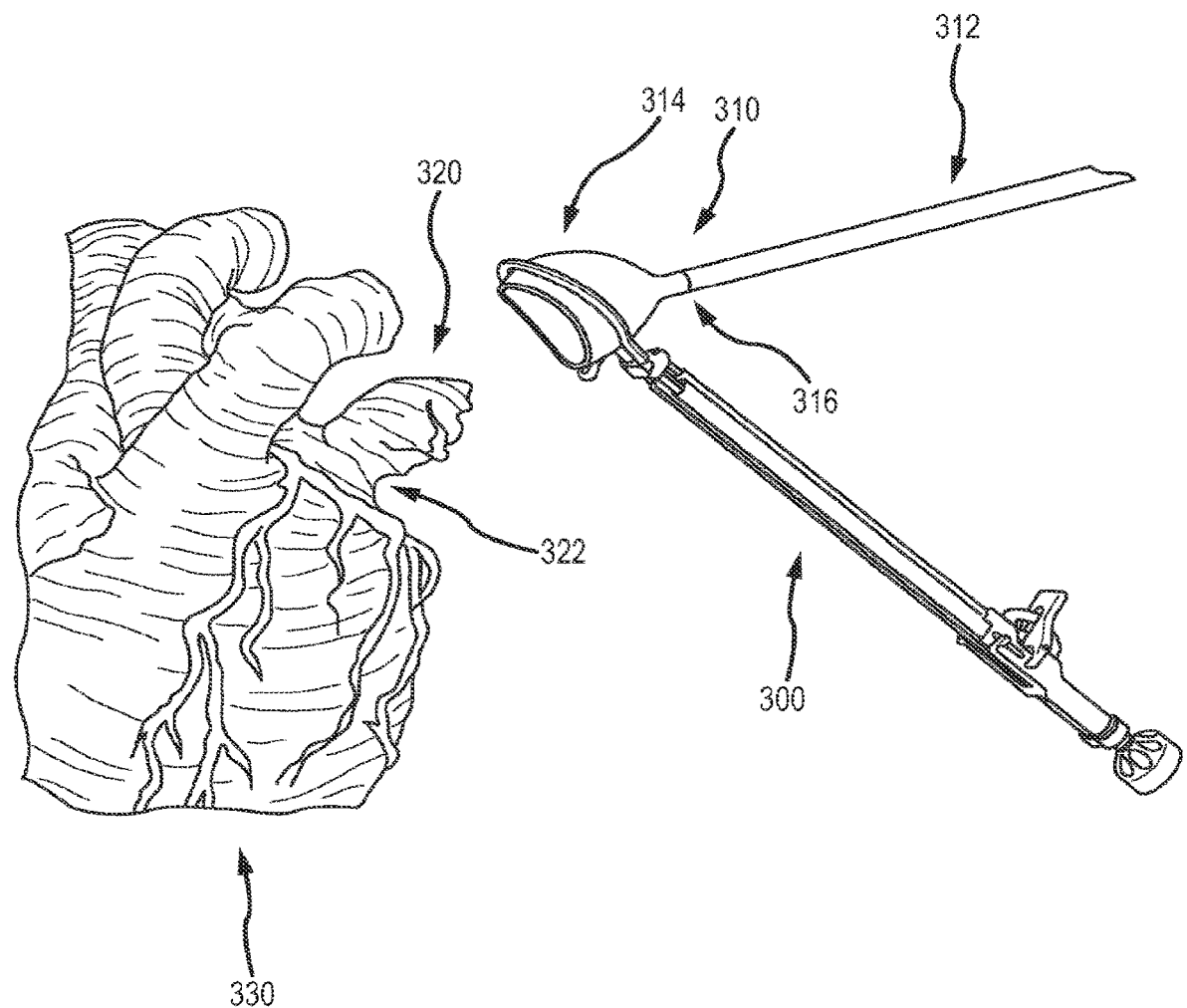
FIGS. 3, 3A, and 3B illustrate aspects of ligature delivery systems and methods according to embodiments of the present invention.

The left atrial appendage (LAA) is a finger like muscular pouch which is connected to and originates supralaterally from the left atrium of the heart. In some cases, the LAA has been referred to as the left auricular appendix, the auricula, or the left auricle. Left atrial appendage occlusion treatments can be an effective means of preventing complications, such as stroke, which may result from atrial fibrillation or eliminate one possible source of aberrant electrical circuits that may originate in the appendage and contribute to atrial fibrillation. FIG. 3 illustrates aspects of a delivery process whereby a ligature thread can be applied to an anatomical feature of a patient. For example, as depicted here, a ligature delivery system 300, optionally in combination with a suction apparatus or grasping means 310, can be used to deliver a ligature thread to a left atrial appendage (LAA) 320 of a patient's heart 330. Accordingly, the applied ligature thread can be used to isolate and occlude the LAA, for example during or as part of an atrial fibrillation treatment procedure. In this way, the applied ligature thread can help to prevent or inhibit negative effects associated with a thromboembolus of the LAA. Typically, the ligature thread loop is applied around the base 322 of the LAA. In many individuals, the circumference at the base 322 of the LAA is within a range from about 4 to about 5 inches. The ligation technique can also be used during or as part of a mitral valve repair procedure. Exemplary grasping means may include suction mechanisms, or other gripping or holding devices such as forceps, clamps, and the like. As shown here, the grasping means 310 can include an elongate handle 312 coupled with a suction cup 314 via a connection 316. In some cases, the handle 312 may be coupled with the suction cup 314 via a jointed connection, such as a ball joint or a hinge joint, or via a deflectable hinge connection or the like. The grasping or suction means 310 may also be integrated into the ligature delivery system so that it enters the patient's body at the same location.

Loading the Delivery System with a Ligature Assembly

Figure 3A:
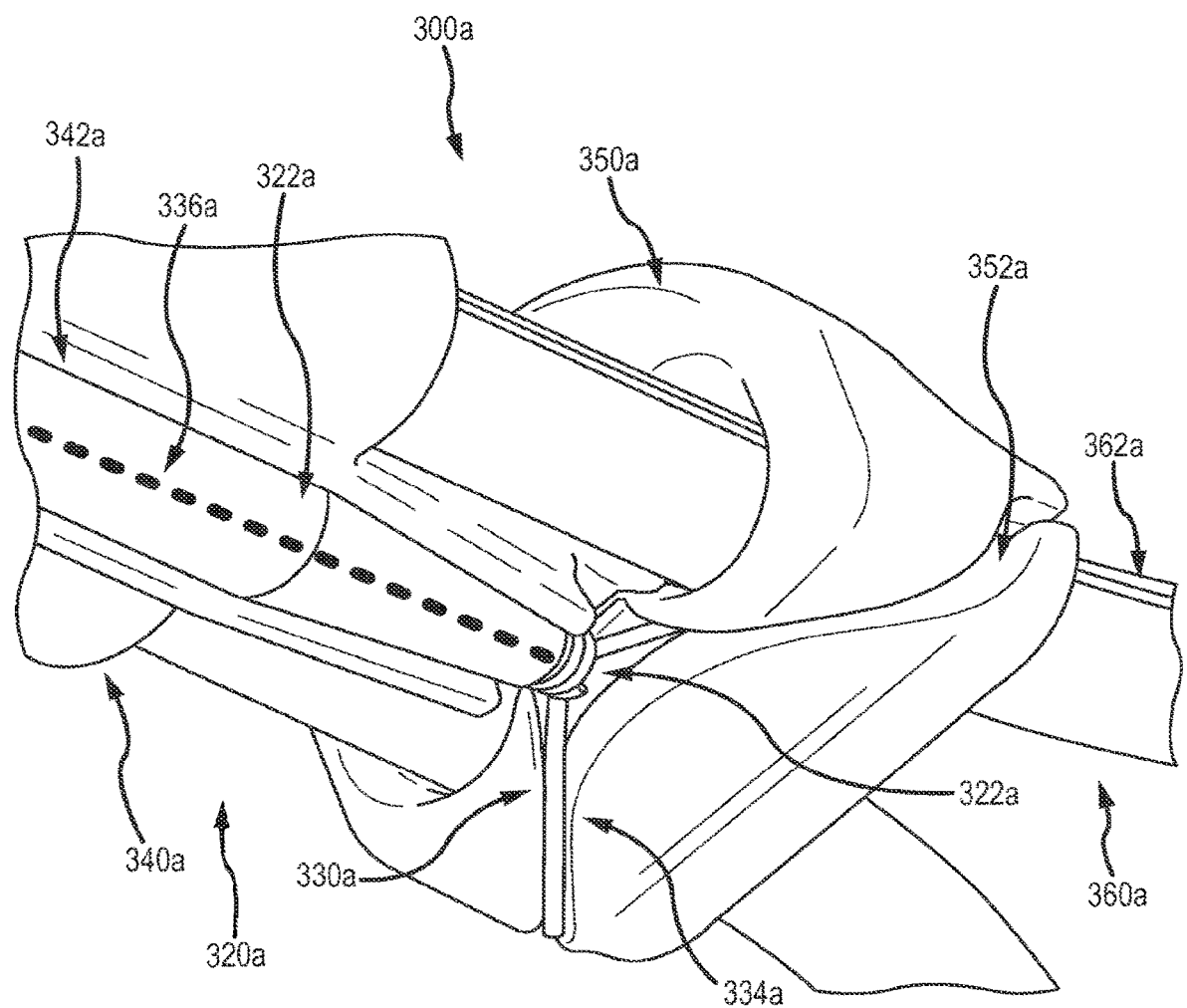

As indicated above, a typical ligature assembly includes a pre-knotted thread having a proximal tail and a distal loop, and a tube carrier disposed about at least a portion of the proximal tail. FIG. 3A depicts a delivery system 300a loaded with a ligature assembly 320a according to embodiments of the present invention. As shown here, the ligature assembly 320a includes a knot pusher or carrier tube 322a and a ligature thread 330a having a knot or one way locking mechanism 332a, a distal loop portion 334a, and a proximal tail portion 336a disposed at least partially within the carrier tube 322a. The delivery system 300a includes a support mechanism 340a having an engagement assembly 342a such as a recess or groove that is configured to receive and releasably attach with the ligature assembly carrier tube 322a. For example, the carrier tube can be snapped or clipped into place within the recess or slot of the support mechanism 340a. The ligature thread distal loop portion 334a can be threaded or routed within or along a groove 352a of a distal deflector body 350a, and also within or along a groove 362a of a thread delivery mechanism or closure delivery means 360a. According to some embodiments, a cinchable loop of the thread delivery mechanism 360a may include a flexible cylinder having a longitudinally extending slot 362a that receives the ligature thread.

Figure 3B:
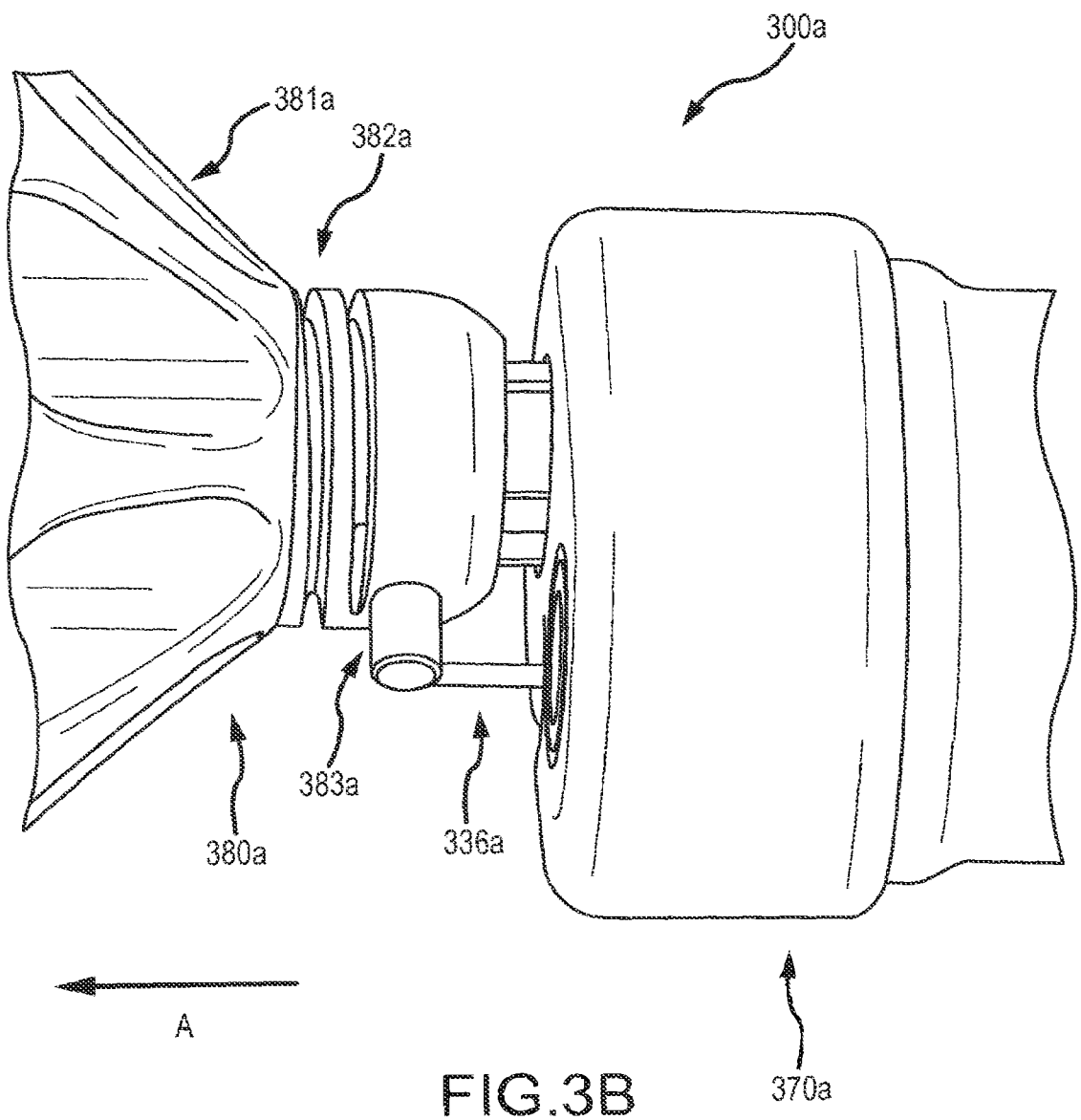
Figure 7A:
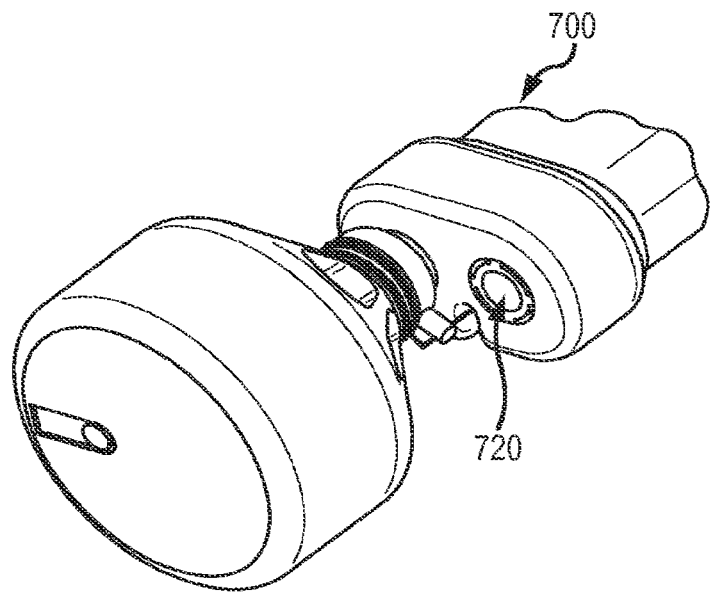
FIGS. 7A to 7D illustrate features of ligature delivery systems and methods according to embodiments of the present invention.
Figure 7B:
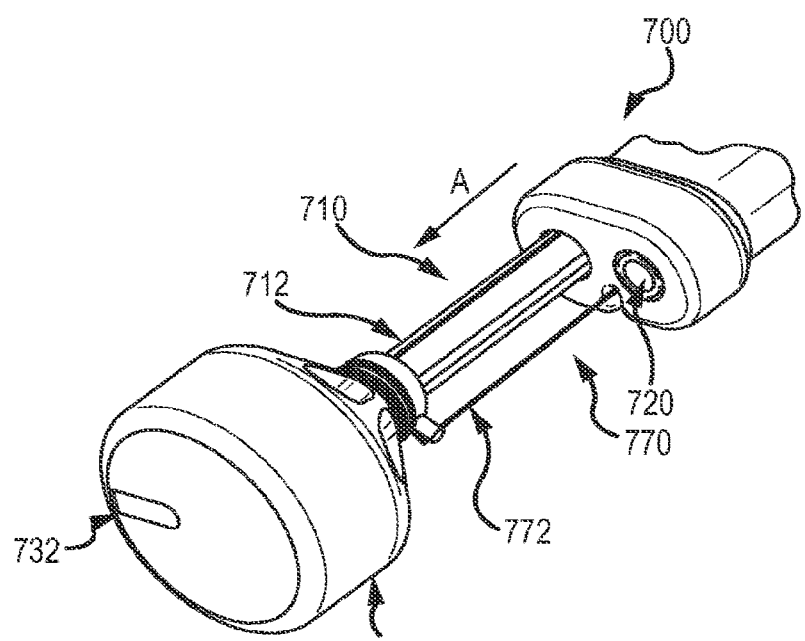
Figure 10A:
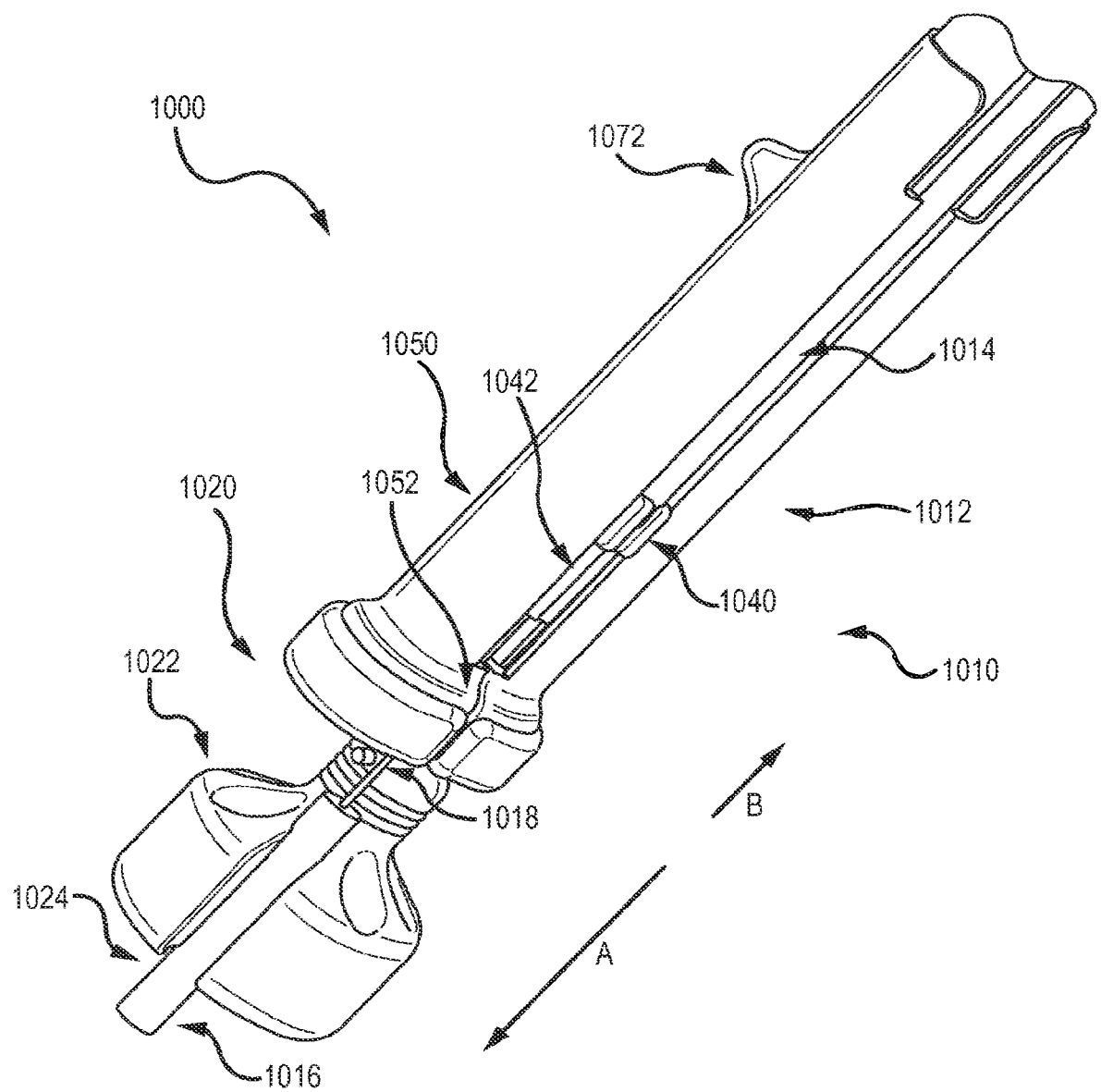
FIGS. 10A, 10B, and 10C show aspects of ligature delivery systems and methods according to embodiments of the present invention.

FIG. 3B shows a side view of a proximal portion of the delivery system 300a. As shown here, a proximal tail portion 336a of the ligature thread extends proximally from the delivery system handle 370a. In use, the proximal tail portion 336a can be wound about a thread holder mechanism 382a of a delivery control mechanism 380a. For example, the surgeon can crack a scored portion of a carrier tube so as to separate a frangible portion from a main body portion, wrap the distal thread loop about the slot 362a of the torqueable carrier tube loop, and then hold the frangible tube portion (as shown in FIG. 2A or 10A) to draw taut the proximal thread portion, and thereafter wind the proximal tail thread portion 336a about the thread holder 382a grooves. In this way, the proximal thread portion can be fixed to the knob. In some instances, the knob or thread holder mechanism 382a may include grooves, wedge cutouts, helical or circular rings or slots, and the like. The operator may wrap the proximal thread portion 336a about the holder mechanism 382a in multiple windings, optionally with thread guide assistance provided by pin 383a (as illustrated in FIGS. 7A and 7B). Hence, one or more thread wrappings or windings can be inserted into one or more grooves or groove sections. Relatedly, thread wrappings or windings can be stacked one upon another. What is more, thread wrappings or windings can be drawn taut relative to the grooves or rings, so as to drive or wedge the threads deeper into the grooves or between rings, so as to lock or fix the proximal thread portion 336a in place, relative to the knob and/or rotary drive. As further explained elsewhere herein, when the proximal tail portion 336a is wound about or otherwise coupled with or fixed to the thread holder mechanism 382a or knob 381a, the delivery control mechanism 380a can be retracted proximally or axially translated in the direction indicated by arrow A relative to the handle 370a, so as to simultaneously contract or cinch both the suture carrier loop and the suture loop (which is mounted on the suture carrier loop). For example, the suture carrier cinchable loop and the thread loop may be constricted or tightened at the same rate. In this way, the cinchable suture carrier loop can be tightened about an anatomical feature while the loop thread remains positioned within a slot or groove of the cinchable loop. Further, the knob 381 can be rotated relative to the handle or support mechanism so as to deliver or adjust a cinchable suture loop, as further discussed elsewhere herein.

In some instances, a physician or operator may use a semi-automated mechanism for loading (and reloading) a suture or closure means onto the cinchable loop. In some instances, a physician or operator may use a hand held instrument for loading (and reloading) a suture or closure means onto the cinchable loop.

Deflection of the Guiding Mechanism Loop Portion

Figure 4A:
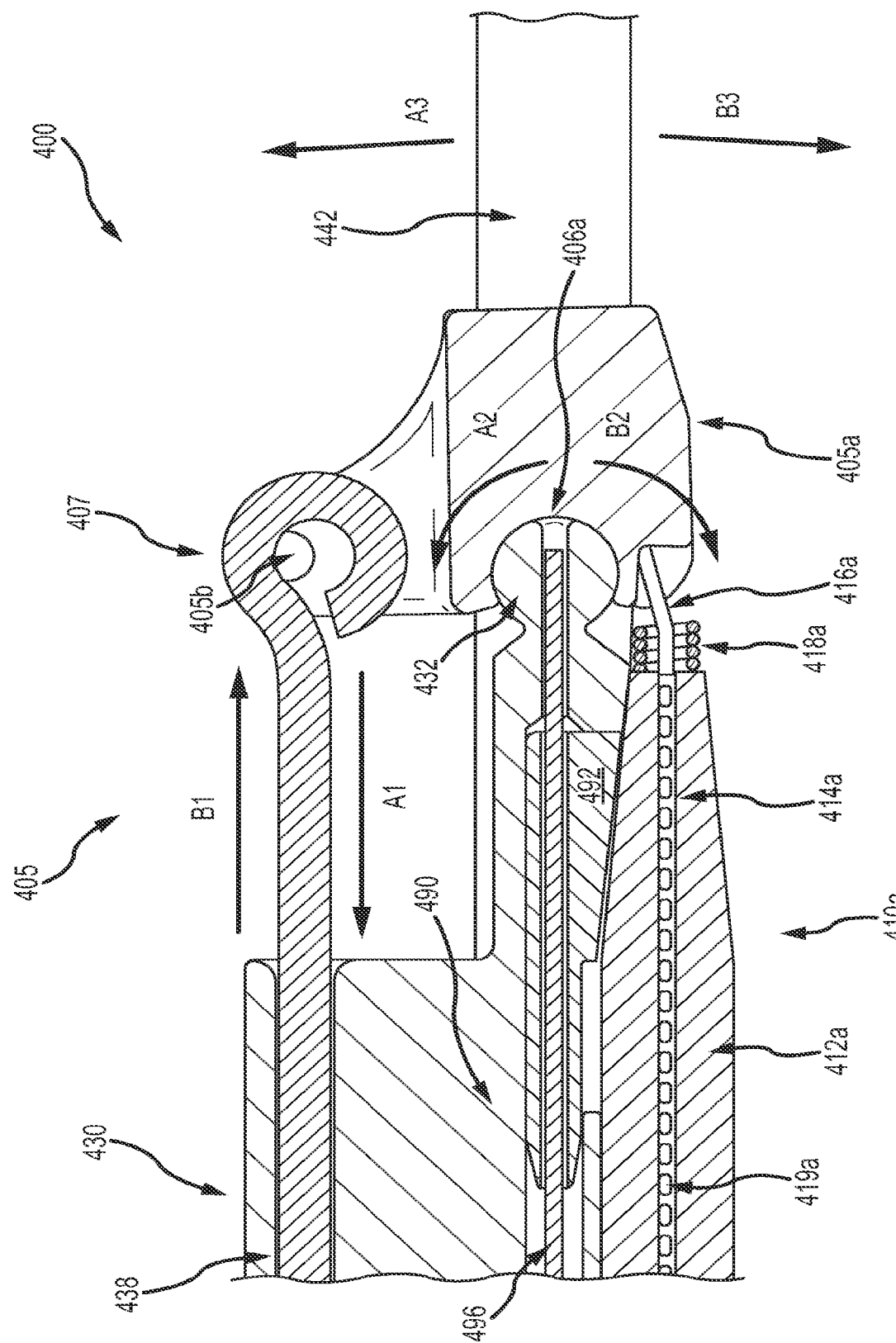

As noted above, the deflection control mechanism can be used to deflect the loop portion of the guiding or thread delivery mechanism. FIG. 4A shows a partial cross-section view of an exemplary ligature delivery system 400 according to embodiments of the present invention. As depicted here, a deflection assembly 405 may include a distal deflector body 405a coupled with a main body or support mechanism 430 of the delivery system 400. In use, the operator can actuate a lever of a deflection control mechanism, which in turn translates a deflection control linkage 407 coupled between the lever (not shown) and the distal deflector body 405a. As shown here, linkage 407 maybe at least partially disposed within or otherwise in operational association with a guide or lumen 438 of the support mechanism 430.

Thus, for example, by actuating the lever so as to retract the linkage 407 proximally as indicated by arrow A1, the linkage 407 pulls a pin 405b of the deflector body in a proximal direction and the distal deflector body 405a rotates relative to a main body pivot 432 as indicated by arrow A2. Consequently, a guiding mechanism loop portion 412 deflects relative to the main body 405a as indicated by arrow A3. Relatedly, by actuating the lever so as to advance the linkage 407 distally as indicated by arrow B1, the linkage 407 pushes the pin 405b of the deflector body in a distal direction and the distal deflector body 405a rotates relative to the main body pivot 432 as indicated by arrow B2. Consequently, the guiding mechanism loop portion 412 deflects relative to the main body 405a as indicated by arrow B3. In this way, a user can flip the main body 405a, and a cinchable loop 442 coupled thereto, in an up-down fashion to provide any desired degree of pitch. Typically, the loop is deflected such that a plane defined by the cinchable loop (and hence a corresponding plane defined by the suture loop portion) is tipped or angled relative to a central longitudinal axis defined by the support mechanism. As shown here, the main body pivot or hinge 432 is shaped as a cylinder, although it is understood that the main body pivot 432 may optionally be shaped as a sphere, so as to provide a ball joint. The deflector mechanism or body 405a includes a corresponding recess or groove 406a that receives the pivot or hinge 432. Any suitable hinge or pivot mechanism may be used to couple the support mechanism 430 with the deflector body 405a. In some cases, the support mechanism and deflector body may be coupled via a living hinge, such that the support mechanism and the deflector body are both part of a single molded or fabricated element, with a thin or flexible connection therebetween.

FIG. 4A also illustrates a ligature assembly 410a engaged with the delivery system 400. As shown here, the ligature assembly 410a includes a carrier tube 412a having a lumen 414a, and a ligature thread 416a having a knot 418a. A proximal tail 419a of the thread is disposed within the lumen 414a, and the knot 418a is disposed distal to a distal end or port of the tube 412a.

Figure 4B:
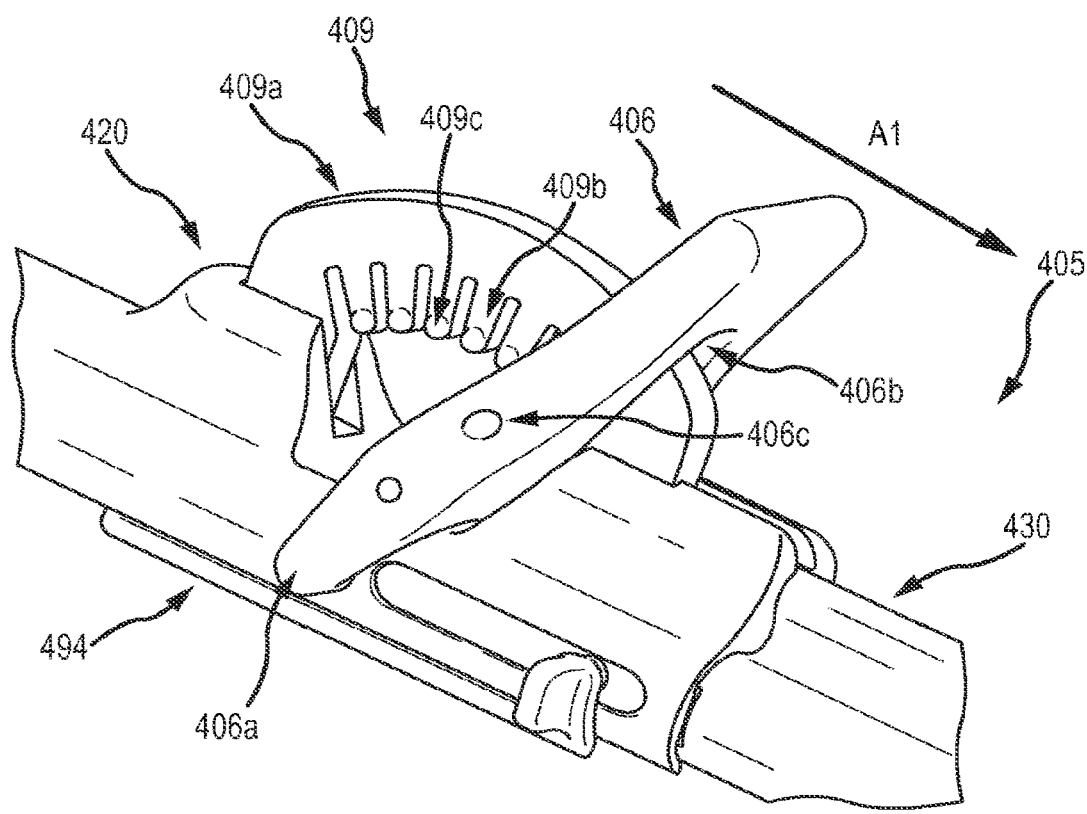
Figure 4C:
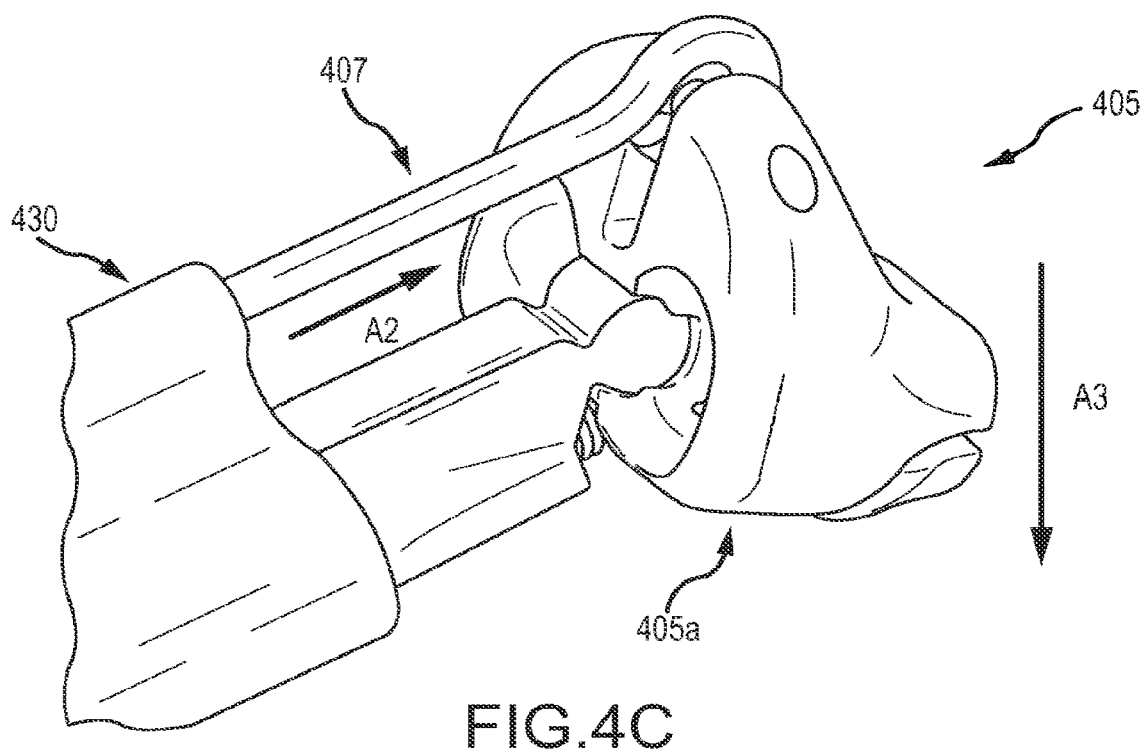
Figure 4D:
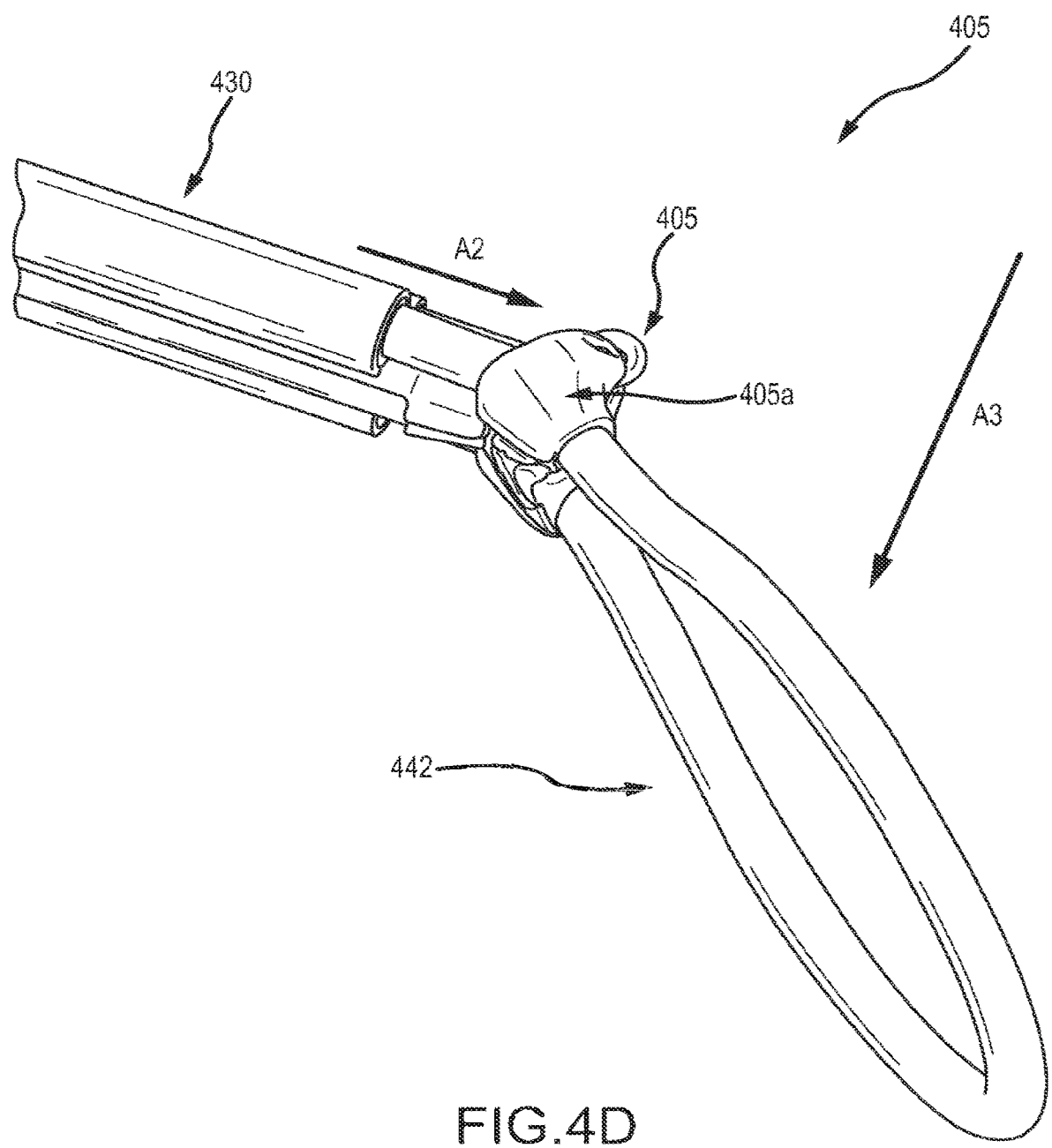

FIGS. 4B, 4C, and 4D depict the deflection assembly 405 in a first or forward deflection configuration. As shown here, a deflection assembly lever 406 of an actuation assembly 409 is moved distal relative to the delivery system handle 420 as indicated by arrow A1, and in a corresponding manner, the deflection assembly linkage 407 is also moved distal relative to the main body 430 as indicated by arrow A2, such that the deflector mechanism or distal deflector body 405a and cinchable loop 442 are pivoted in a downward direction as indicated by arrow A3. The actuation assembly 409 may include an arch or support 409a having multiple flexible fingers 409b with protruding beads 409c, which can releasably engage and hold lever 406 at any of a series of discrete angled orientations relative to the support mechanism. Hence, as the lever 406 is pivoted distally as indicated by arrow A1, the lever angularly rotates about a pivot mechanism 406a, and a slot 406b of the lever moves distally relative to the support 409a. A hole or recess 406c of the lever sequentially receives or engages the individual finger protrusions 409c as the lever moves, with the protrusions 409c popping into and out of the recess 406c. The engagement between the finger protrusions 409c and the lever recess 406c provide physical interference so that the lever can be moved incrementally at discrete angular positions relative to the support mechanism 430.

Figure 4E:
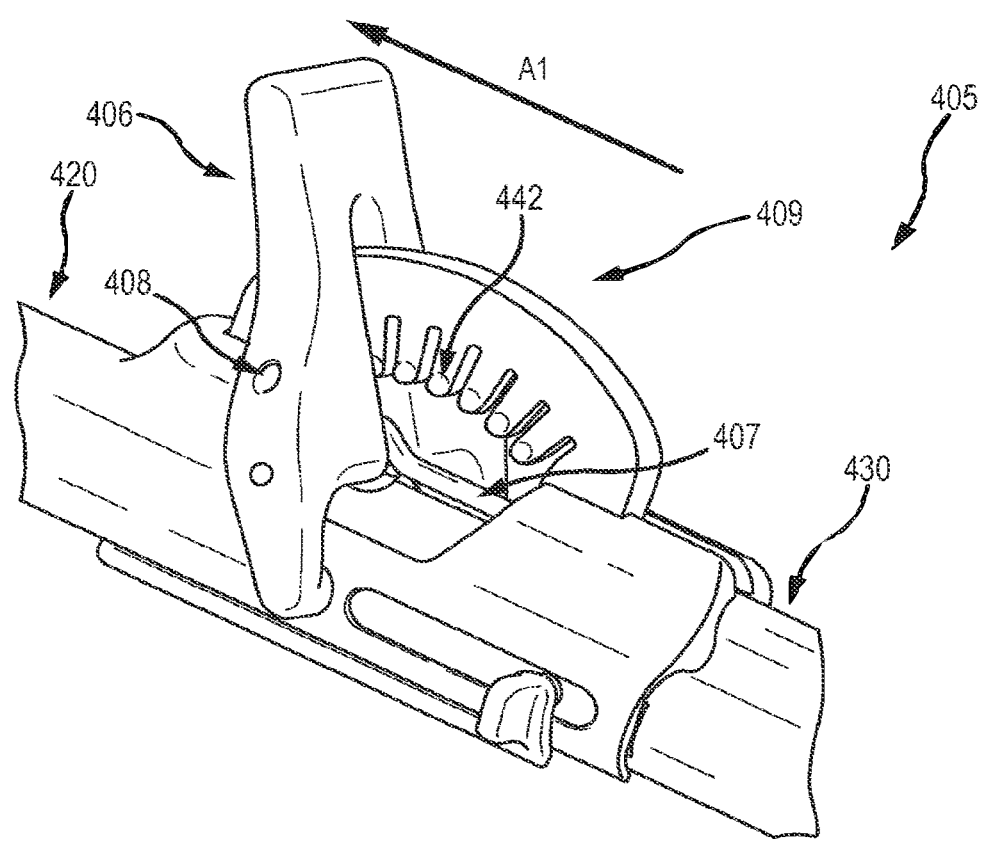
Figure 4F:
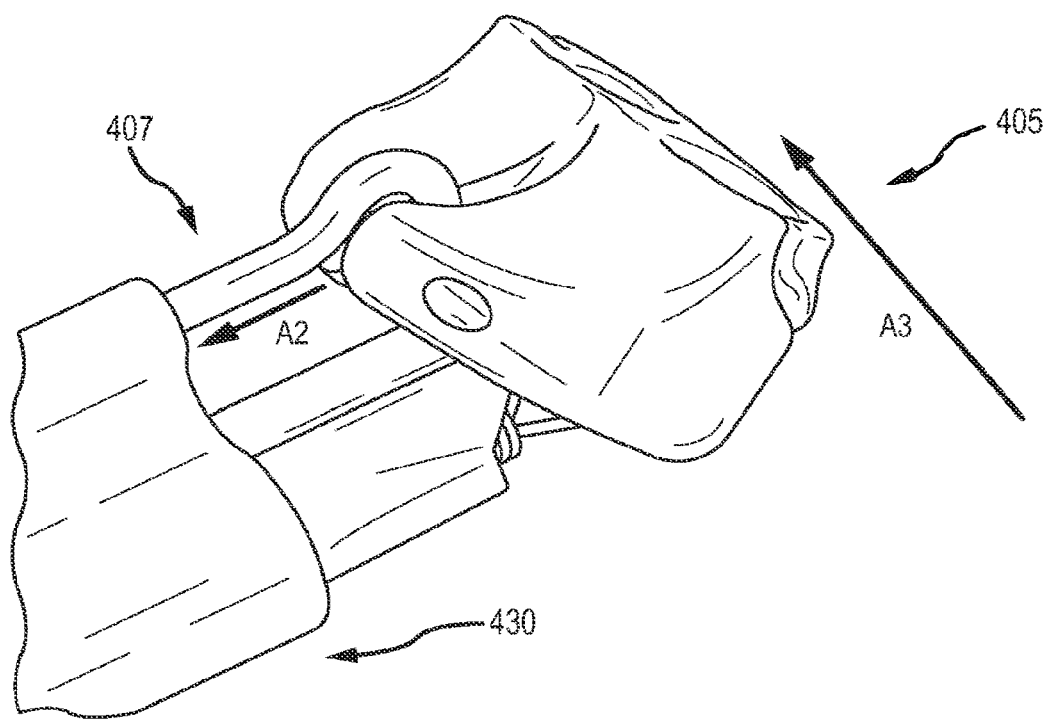

FIGS. 4E, 4F, and 4G depict the deflection assembly 405 in a second or reverse deflection configuration. As shown here, a deflection assembly lever 406 of the actuation assembly 409 is moved proximal relative to the delivery system handle 420 as indicated by arrow A1, and in a corresponding manner, the deflection assembly linkage 407 is also moved proximal relative to the main body 430 as indicated by arrow A2, such that distal deflector body 405a and cinchable loop 442 are pivoted in an upward direction as indicated by arrow A3. In some instances, the support mechanism 430 or handle 420 includes a series of stops or engagement features 422 which can engage a corresponding recess or engagement feature 408 of the lever 406, such that the linkage 407 can be incrementally translated or adjusted relative to the support mechanism, thereby provided discrete pitch adjustments for the cinchable loop.

Lateral Movement of the Guiding Mechanism Loop Portion

Figure 5:
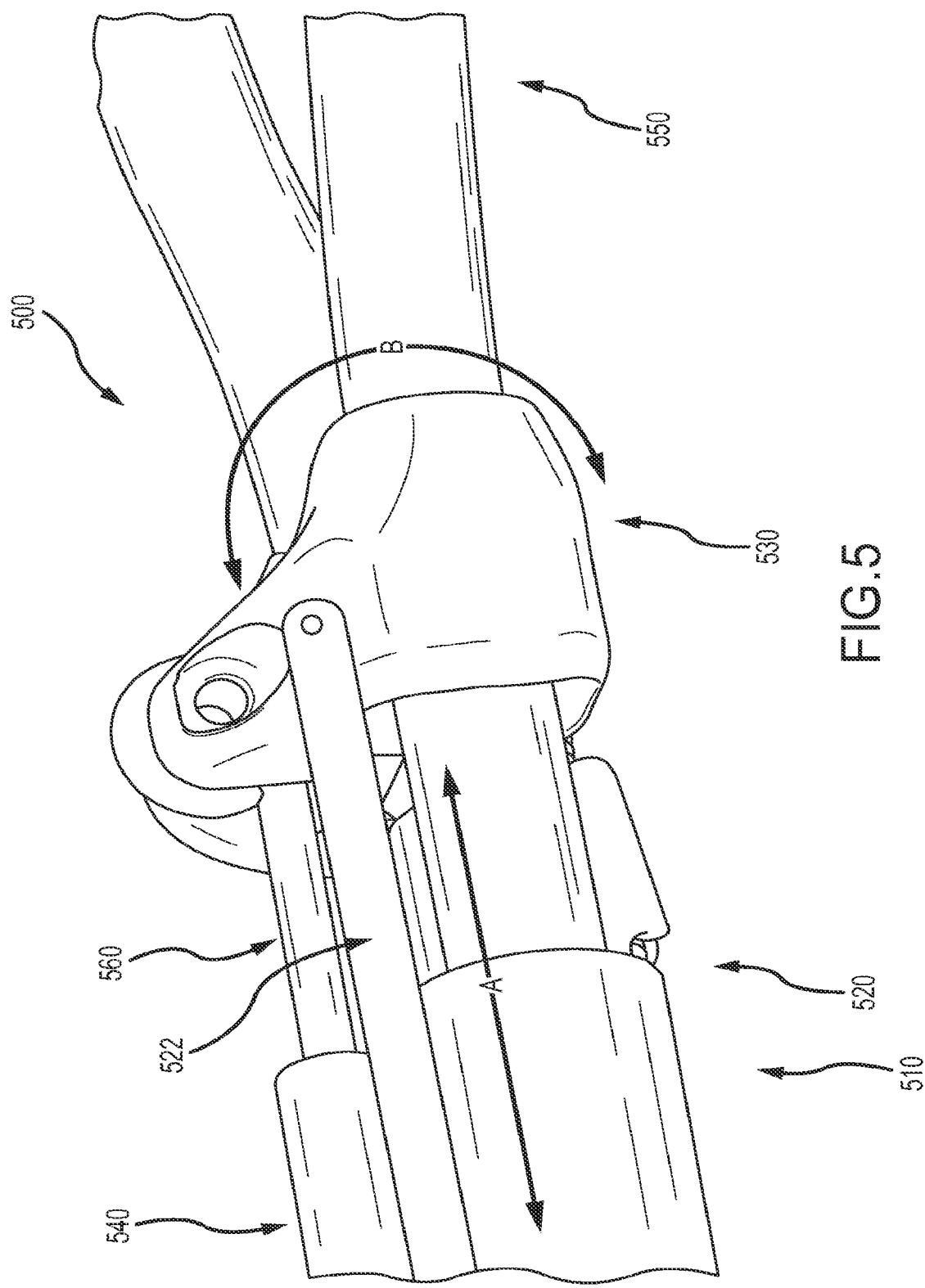
FIG. 5 depicts aspects of ligature delivery systems and methods according to embodiments of the present invention.

As depicted in FIG. 5, a ligature delivery system 500 may include a deflection control mechanism 510 that, in addition to or in place of a pitch control assembly as illustrated in FIGS. 4A to 4G, also includes a yaw control assembly 520. For example, the yaw control assembly may include a linkage or push-pull rod 522 coupled with the deflector mechanism 530, such that proximal and distal translational movement of the linkage 522 relative to the support mechanism 540 as indicated by arrow A, operates to deflect or pivot the deflector mechanism 530 in a side-to-side fashion as indicated by arrow B. To facilitate such pivoting yaw movements, the ligature delivery system may include a hinge or pivot (e.g. such as a ball joint) disposed between and connecting the support mechanism with the deflector mechanism. A similar hinge or pivot (e.g. such as a ball joint) can be disposed between the pitch control linkage 560 and the deflector mechanism. In some cases, the yaw control assembly may include two parallel linkages or push-pull rods. So, for example, a first linkage may advance distally while a second linkage retracts proximally, the coordinated action between these two linkages operates to rotate the deflector mechanism (and hence the cinchable loop 550) in a yaw direction as indicated by arrow B. Alternately, if a particular yawed, or sideways disposed position is desired for the cinchable loop, the distal assembly may have a bend permanently designed into its shape, and the ligature delivery system may not include control linkages and hinges or ball joints as described above. In yet another embodiment, the deflector body or mechanism may be moveable as described above, for example with control linkages and hinges or ball joints, and the hinge or ball joint connection may include an offset or angular alignment orientation so as to dispose the deflector body or mechanism to one side or up or down in a nominally offset position from the long axis of the main delivery device body or support mechanism.

Guiding the Ligature Loop to the Anatomical Feature

Figure 6:
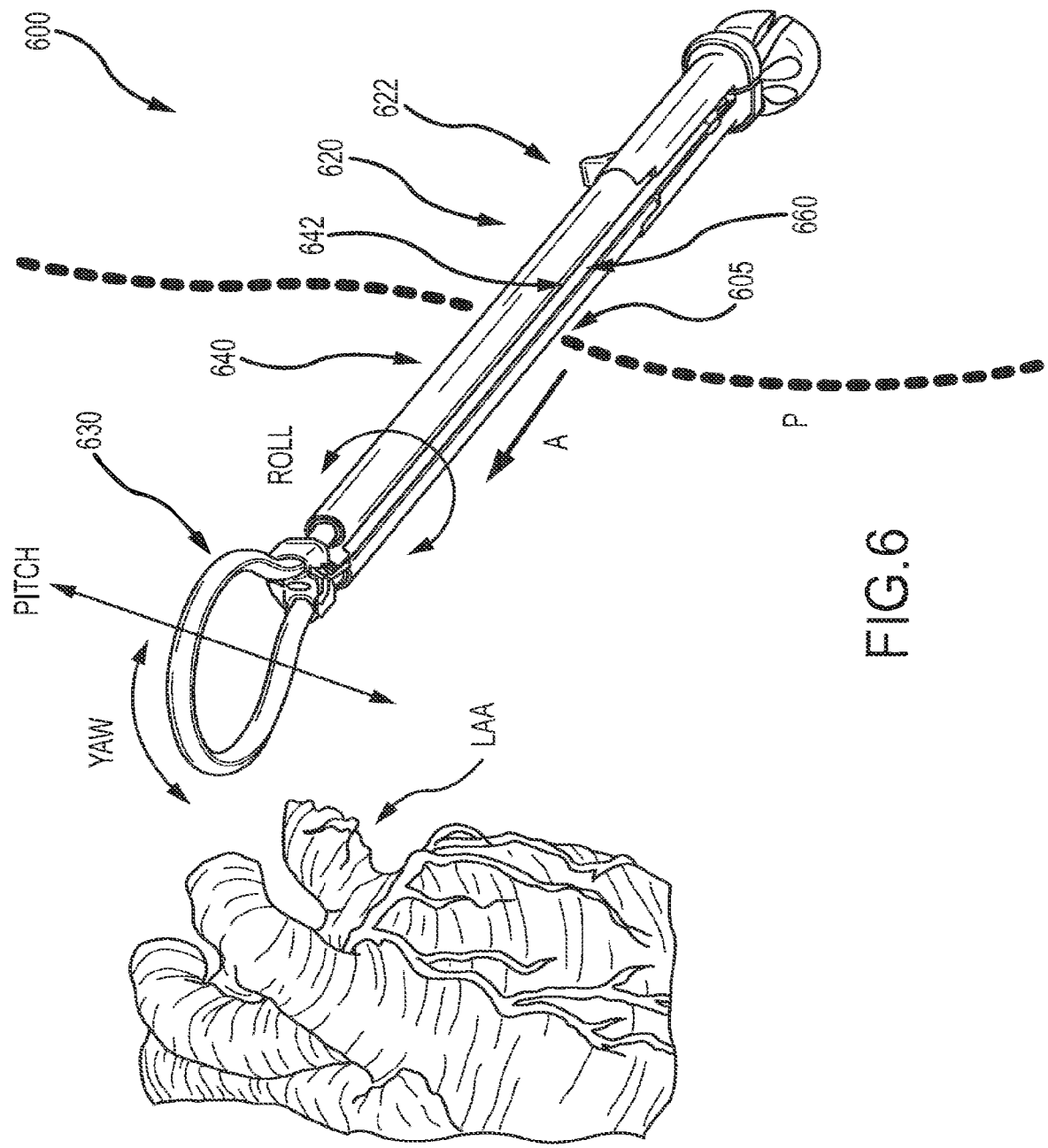
FIG. 6 depicts aspects of ligature delivery systems and methods according to embodiments of the present invention.

In use, the distal portion of a ligature delivery system 600 can be delivered or introduced through a patient access location 605 of a patient P, in the direction indicated by arrow A, as illustrated by FIG. 6. In some cases, the access location 605 may be provided by a thoracotomy in the left side of the patient's body. For example, the access location 605 may be provided by a port access between the ribs on the left side of the patient's chest. By actuating one or more levers or control sliders 622 of a deflection control mechanism 620, and/or by rotating the support mechanism 640 about its central longitudinal axis, the operator can adjust the orientation of the cinchable loop 630 to any desired degree of pitch, yaw, or roll, thus aligning the loop for facile placement about the anatomical structure (e.g. left atrial appendage or LAA). In some instances, the device may be configured to pivot throughout a pitch range of 180 degrees. Hence, the maneuverability of the ligature delivery system allows the surgeon or operator to align a plane defined by the ligature thread loop in any desired orientation. For example, the plane defined by the ligature thread loop can be aligned with a plane defined by the base of the left atrial appendage, thus promoting facile application of the ligature snare to the left atrial appendage. In this way, the operator or surgeon can adjust the plane of the suture loop to any desired orientation related to the patient's anatomy (e.g. the base of the left atrial appendage). As further discussed elsewhere herein, the ligature delivery assembly may include or be used in cooperation with a tissue grasping assembly such as a suction cone assembly, a forceps assembly, or the like, which can be used to positionally manipulate the patient tissue relative to the ligature thread loop or cinchable loop carrier.

In some cases, a patient administration modality may be achieved through a port access, a sternotomy access, a thoracotomy access, a subxyphoid access, a subcostal access, a transdiaphragmatic access, or the like. In some instances, the support mechanism 640 may be constructed to include a curved configuration or portion, which may provide additional benefits during a subxyphoid access procedure, for example. In some instances, portions of the system such as a support mechanism may be manufactured with a pre-formed curve. In some instances, portion of the system such as the support mechanism may be manufactured to include a flexible or bendable section. In some cases, access may be achieved with the ligature delivery system 600 during a concomitant surgical procedure such as an atrial fibrillation ablation procedure, a bypass surgery procedure, a valve surgery procedure, or the like.

As shown here, the support mechanism 640 can engage with a carrier tube 660 of a ligature assembly. Optionally, where a ligature assembly does not include a carrier tube, the proximal tail portion of the ligature thread can be placed along or within an engagement member or guide 642 of the support mechanism. The engagement member or guide 642 can be sized or configured to accommodate or receive carrier tubes of any suitable length, diameter, cross-section shape, or configuration. Similarly, the engagement member or guide 642 can be sized or configured to accommodate or receive ligature threads of any suitable length, diameter, cross-section shape, or configuration.

Sizing the Ligature Loop to the Anatomical Feature

When the suture thread loop and the cinchable loop of the thread delivery mechanism are positioned as desired, the delivery system can be actuated so as to simultaneously contract or cinch the delivery mechanism and suture loops about an anatomical feature. For example, as depicted in FIGS. 7A to 7E, the delivery control mechanism 700 may include a first rotary drive or translating suture carrier support 710 and a second rotary drive or fixed suture carrier support 720. In some instances the first rotary drive 710 is disposed within a first lumen or engagement mechanism of the support mechanism 760. In some cases the second rotary drive 720 is disposed within a second lumen or engagement mechanism of the support mechanism. Hence, the support mechanism may be considered to include an engagement assembly (e.g. which includes the first and second lumens) that couples with a delivery control mechanism. The translating rotary drive 710 includes a proximal portion 712 coupled with a control knob 730 that can be retracted proximally out of the handle 740 as indicated by arrow A. The translating rotary drive 710 also includes a distal portion 714 coupled with a translating portion 752 of the thread delivery mechanism 750 that can be retracted proximally into the support mechanism 760. As shown here, a proximal tail portion 772 of a ligature thread 770 can be fixed relative to the control knob 730, and thus drawn proximally when the knob is drawn proximally. A broken-off frangible portion (not shown) of the carrier tube may be dangling from a proximal end of the thread tail 722. Alternatively, the frangible portion may be pushed into a wedge shaped groove in the control knob 730, the slack in the suture being taken up by the lengthwise position of the frangible portion in the groove. Hence, when knob 730 is drawn proximally, the first rotary drive 710 is drawn proximally as indicated by arrows A, the thread delivery mechanism translating portion 752 is drawn proximally as indicated by arrow B, thus cinching the loop 750, and a ligature thread loop translating portion 772 (which is connected with the knob via the thread proximal tail) is also drawn proximally as indicated by arrow C, and through the suture knot, thus cinching the ligature loop. As shown here, as translating portion 772 of the ligature thread is drawn proximally, it continually exits a groove 755 of the thread delivery mechanism 750 at a moving peel-off point 756. In this way, the thread delivery mechanism 750 moves in conjunction with the ligature thread 770, such that both elements can be simultaneously cinched about a desired anatomical feature. As the translating portion 759 of the cinchable loop is drawn across the patient tissue, the cinchable loop operates to protect the tissue which would otherwise be in contact with the translating portion 772 of the ligature thread. More generally, the cinchable loop operates to protect or shield the patient tissue from the suture thread, until such a time that the suture thread is delivered to the patient tissue (e.g. by rotating the cinchable loop, as described elsewhere herein). The non-translating rotary drive 720 includes a distal portion 722 coupled with a similarly non-translating portion 754 of the thread delivery mechanism 750, in that the rotary drive 720 and the non-translating portion 754 do not translate relative to the support mechanism. As described elsewhere herein, a push-pull rod or linkage 780 can operate to deflect a deflector mechanism 790. In some instances, a knob 730 may include an orientation indicator 732, so that an operator or user can visualize the rotational orientation of the knob, and thus be aware of the corresponding rotational orientation of the rotary drives and the cinchable loop. In some cases, the orientation indicator 732 may represent the position of the carrier tube groove, the position of the thread disposed within the carrier tube groove, the position of the groove in the translating portion 752 of the delivery mechanism 750, or the position of the thread in the translating portion 752 (e.g. relative to the central longitudinal axis of the carrier tube or first rotary drive). In this way, the surgeon may know whether or not the thread delivery mechanism is in a configuration suitable for delivering the ligature thread to the anatomical structure. In an additional but related embodiment, the delivery system may be designed such that when the cinchable carrier loop 750 is cinched onto the target tissue, the suture loop moves with the cinchable loop 750, thus protecting the tissue, but the suture loop is not actually cinched tight until after the carrier loop 750 is tight. This can be accomplished by pulling both sides of the carrier loop 750 into the support mechanism 760 simultaneously, for example by drawing the first rotary drive 710 and the second rotary drive 720 in a proximal direction, and also moving the ligature assembly carrier tube and the ligature knot in a proximal direction, thus allowing the suture loop to also move proximally. When the carrier loop 750 is sufficiently tight, the suture loop can be tightened, for example by moving the ligature assembly carrier tube or knot pusher in a distal direction so as to advance the knot in a distal direction, while optionally pulling or retracting a frangible portion of the ligature assembly in a proximal direction. In this way, the advancing knot, with the carrier tube backing it up, can approach and contact the tissue. The circumferential cinching force can be transferred from the carrier loop 750 to the suture, but because this happens at the last moment, there is no slicing action against the tissue by the suture loop. The delivery system can then unload or deploy the suture and be removed.

Delivering the Ligature Loop to the Anatomical Feature

Figure 7C:
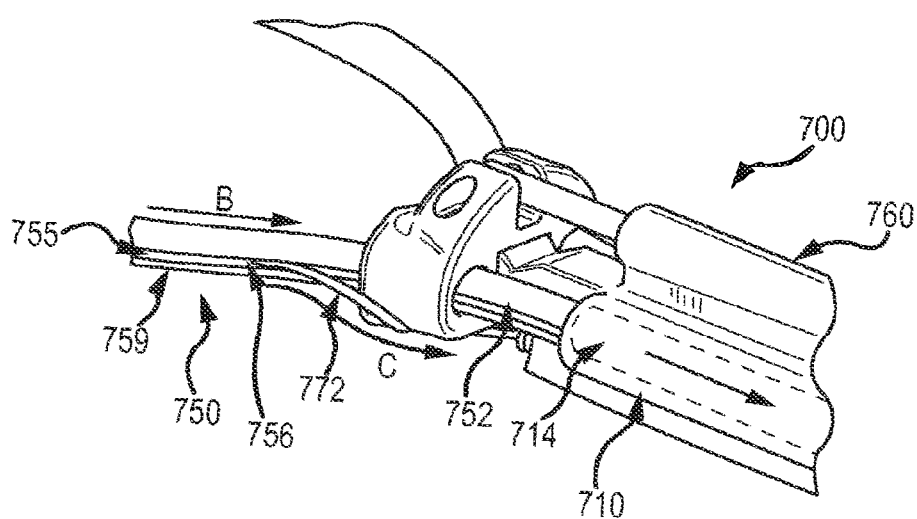
Figure 7D:
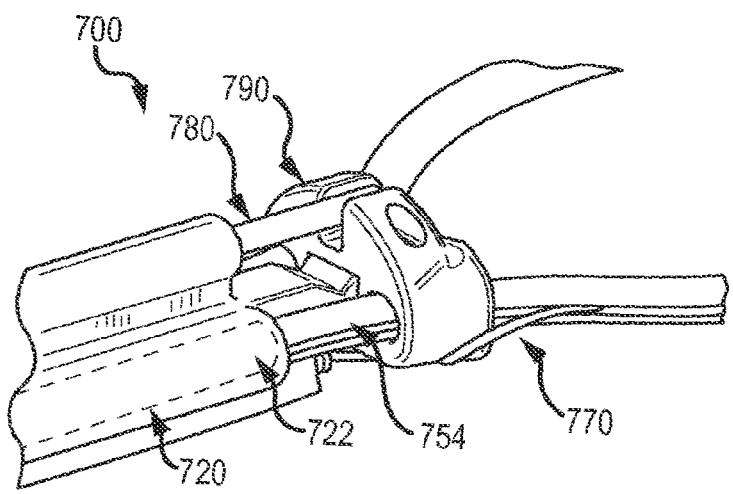
Figure 8A:
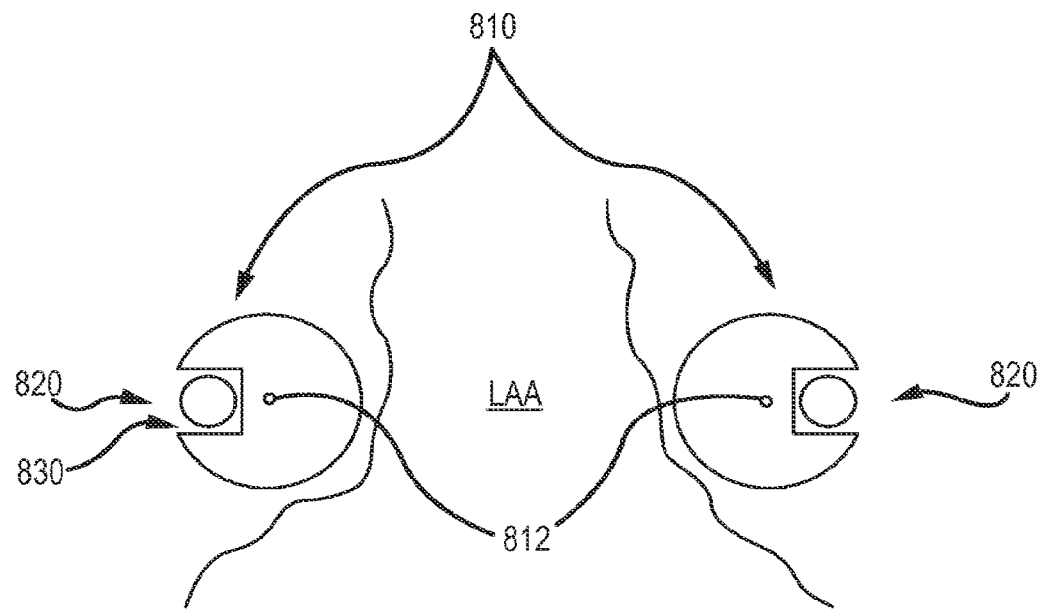
FIGS. 8A to 8J show aspects of ligature delivery systems and methods according to embodiments of the present invention.
Figure 8B:
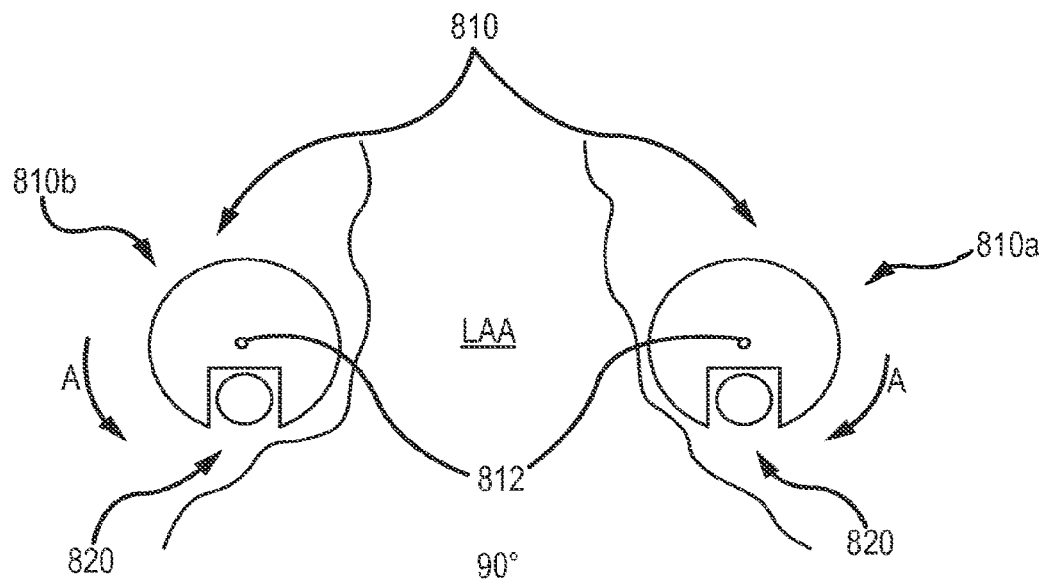

As depicted in FIGS. 7C and 7D, the thread disposed within the slot of the cinchable loop portion can be shielded from the ensnared anatomical feature. For example, as illustrated in the cross-section view of FIG. 8A, the left atrial appendage (LAA) is encircled by a cinchable loop 810 of a ligature delivery system. The cinchable loop can rotate about a central longitudinal axis 812, as indicated by arrows A. In this way, the cinchable loop can switch between a first configuration where the thread 820 is shielded from the left atrial appendage, as shown in FIG. 8A, and a second configuration where the thread 820 can be released onto the base of the left atrial appendage, as shown in FIG. 8B.

Figure 8C:
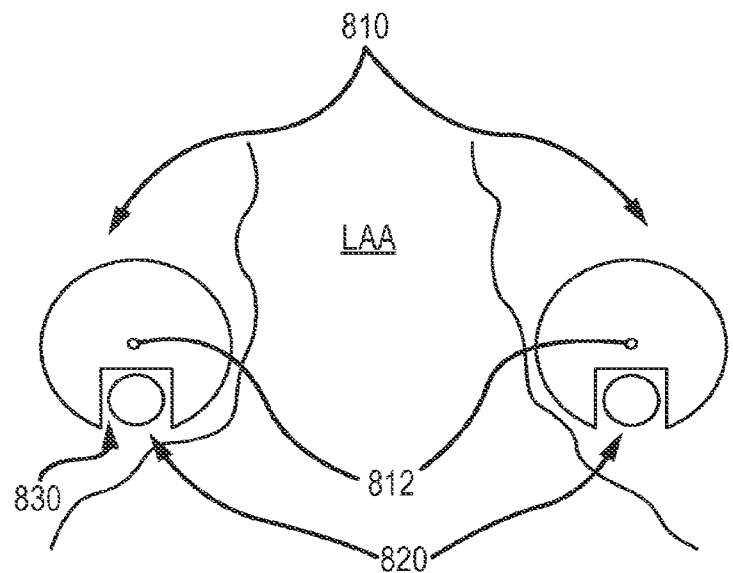
Figure 8D:
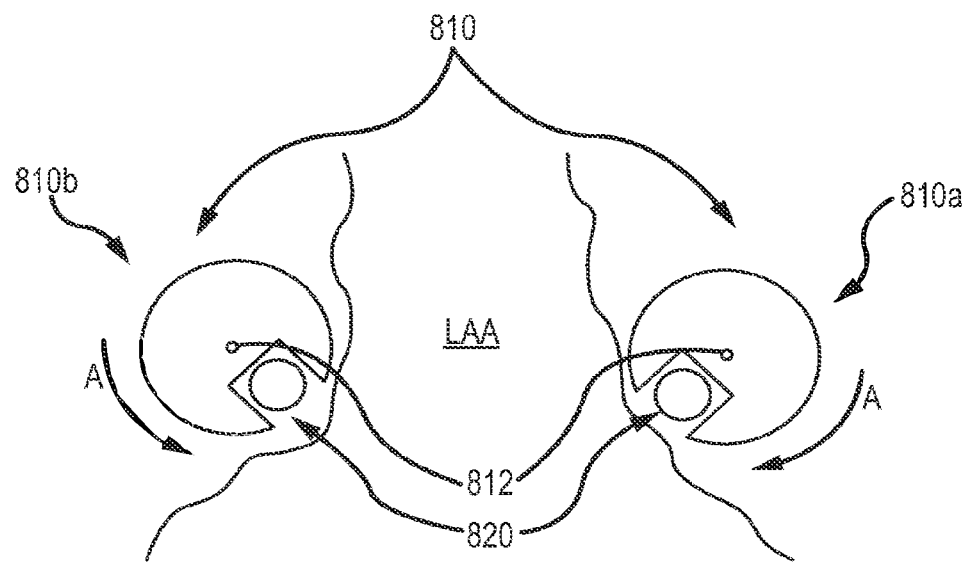

Similarly, as illustrated in the cross-section view of FIG. 8C, the left atrial appendage (LAA) is encircled by a cinchable loop 810 of a ligature delivery system. The cinchable loop can rotate about a central longitudinal axis 812, as indicated by arrows A. For example, the slot 830 of the cinchable loop can be rotated toward the appendage by about 10 to 15 degrees. It is understood that any suitable angular rotation of the cinchable loop may be performed so as to deliver the thread or suture to the desired location. In this way, the cinchable loop can switch between a first configuration where the thread 820 is shielded from the left atrial appendage, as shown in FIG. 8C, and a second configuration where the thread 820 can be released onto the base of the left atrial appendage, as shown in FIG. 8D. Hence, in some cases the suture may be facing outward away from the left atrial appendage as the cinchable loop is tightened. In other cases, the suture may be facing downward toward the base of the left atrial appendage as the cinchable loop is tightened. It is therefore understood that the suture may be facing in any desired direction relative to the left atrial appendage as the cinchable loop is maneuvered and/or constricted. Typically, the groove or slot 830 will be oriented such that the left atrial appendage is shielded from the suture as the loop tightens, which can help to protect the left atrial appendage (or other any other anatomical structure or tissue to which a ligature is applied) from being damaged as the ligature is tightened or constricted about the tissue. In some instances, the applicator system may be configured to decouple the occlusive member from the applicator upon delivery of the occlusive member so as to minimize potential for tissue trauma.

Figure 8E:
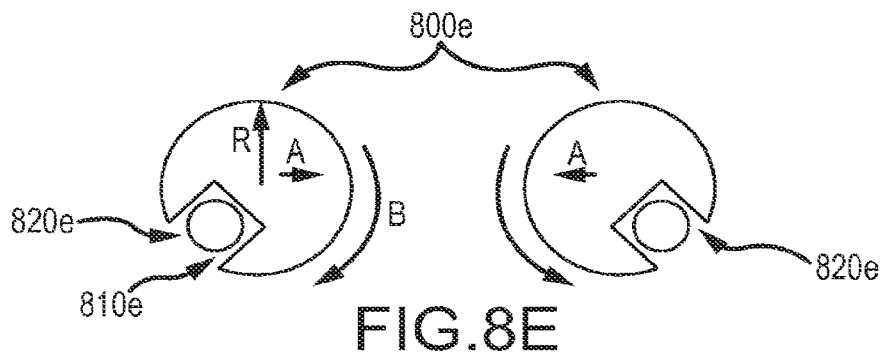

FIG. 8E depicts another thread delivery mechanism configuration according to embodiments of the present invention. As shown in this cross-section view of a cinchable loop 800e, the slot or groove 810e presents an offset angle relative to radius R of the loop cylinder. Biasing the slot 810e at a different angle, offset relative to the center of the carrier cylinder, may enable the effect of tightening the suture to assist in the rotation of the suture carrier. For example, as shown here, tightening the suture thread loop 820e within the groove as indicated by arrow A, may result in application of a rotational force to the loop 800e as indicated by arrow B. Relatedly, the biased slot may it may assist in retaining the suture thread 820e in the groove until the suture carrier or thread delivery mechanism has rotated significantly inward. If there is sufficient traction between the tissue and the loop, however, the rotation indicated by arrow B may operate to move the loop away from an intended target (e.g. the base of the left atrial appendage), or to pull the tissue downward through the cinchable loop, placing the suture high on the anatomy (e.g. far away from the base of the base of the left atrial appendage).

Figure 8F:
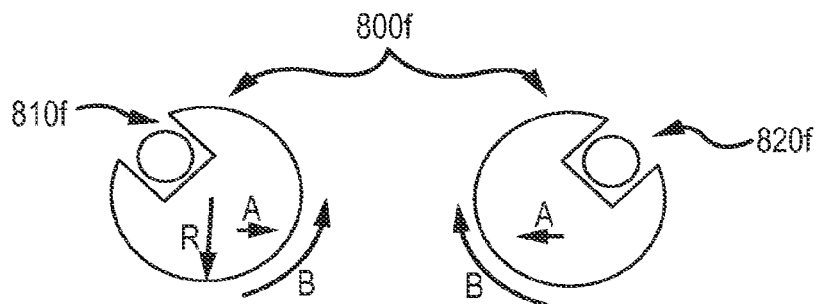

FIG. 8F depicts another thread delivery mechanism configuration according to embodiments of the present invention. As shown in this cross-section view of a cinchable loop 800f, the slot or groove 810f presents an offset angle relative to radius R of the loop cylinder. Biasing the slot 810f at a different angle, offset relative to the center of the carrier cylinder, may enable the effect of tightening the suture to assist in the rotation of the suture carrier. For example, as shown here, tightening the suture thread loop 820f within the groove as indicated by arrow A, may result in application of a rotational force to the loop 800f as indicated by arrow B. Relatedly, the biased slot may it may assist in retaining the suture thread 820f in the groove until the suture carrier or thread delivery mechanism has rotated significantly inward.

Figure 8G:
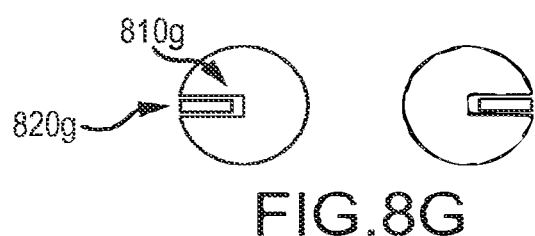

FIG. 8G depicts another thread delivery mechanism configuration according to embodiments of the present invention. As shown here, a thread delivery mechanism may include a deeply recessed narrow groove 810g that is shaped to receive a band or ribbon suture thread 820g in a radially aligned orientation.

Figure 8H:
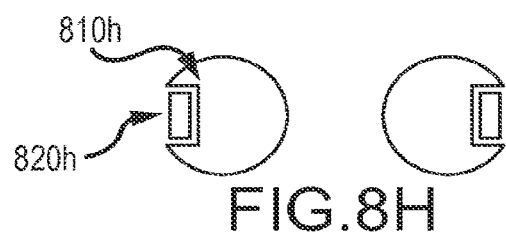

FIG. 8H depicts another thread delivery mechanism configuration according to embodiments of the present invention. As shown here, a thread delivery mechanism may include a shallowly recessed broad groove 810h that is shaped to receive a band or ribbon suture thread 820h in a tangentially aligned orientation.

Figure 8I:
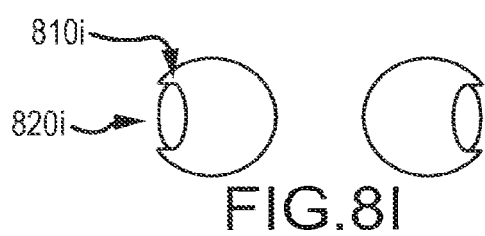

FIG. 8I depicts another thread delivery mechanism configuration according to embodiments of the present invention. As shown here, a thread delivery mechanism may include an ovalized groove 810i that is shaped to receive an ovalized suture thread 820i.

Accordingly, embodiments of the present invention encompass any of a variety of slot or groove shapes or configurations, as well as various thread shapes and sizes. As can be seen in FIGS. 8A to 8I, firm cinching force can be applied to a suture thread or other ligature filament, such that a portion of the thread loop is drawn through a knot without sliding against the patient's tissue. In this way, ligature thread loops can be applied to the patient anatomy with a significantly reduced risk of cutting the tissue with the tightening thread. In some instances, a ligature thread may have a thickness of about 15 to about 20 thousandths of an inch. Embodiments of the present invention provide techniques for tightening such threads about patient tissue features, while protecting the tissue from severing effects that the thread may otherwise have on the tissue. For instance, where a ligature thread includes a one-way knot with a distal loop, upon tightening of the thread, one portion of the loop remains fixed relative to the knot, and another portion of the loop slides through the knot. Use of the presently described systems and methods allows the surgeon or user to translate the sliding loop portion through the knot, while placed under significant compressive forces, without having the sliding thread cut into or otherwise damage or compromise the patient tissue. In some instances, a ligature delivery system is provided as a single-patient use device, whereby a surgeon or operator can use the delivery system as desired to deliver one or more ligature threads to the patient anatomy. In some instances, a user or operator can use the delivery system to apply multiple ligature loops to a single anatomical feature, thus for example spreading out or otherwise distributing the compressive forces applied to the anatomical feature.

Figure 8J:
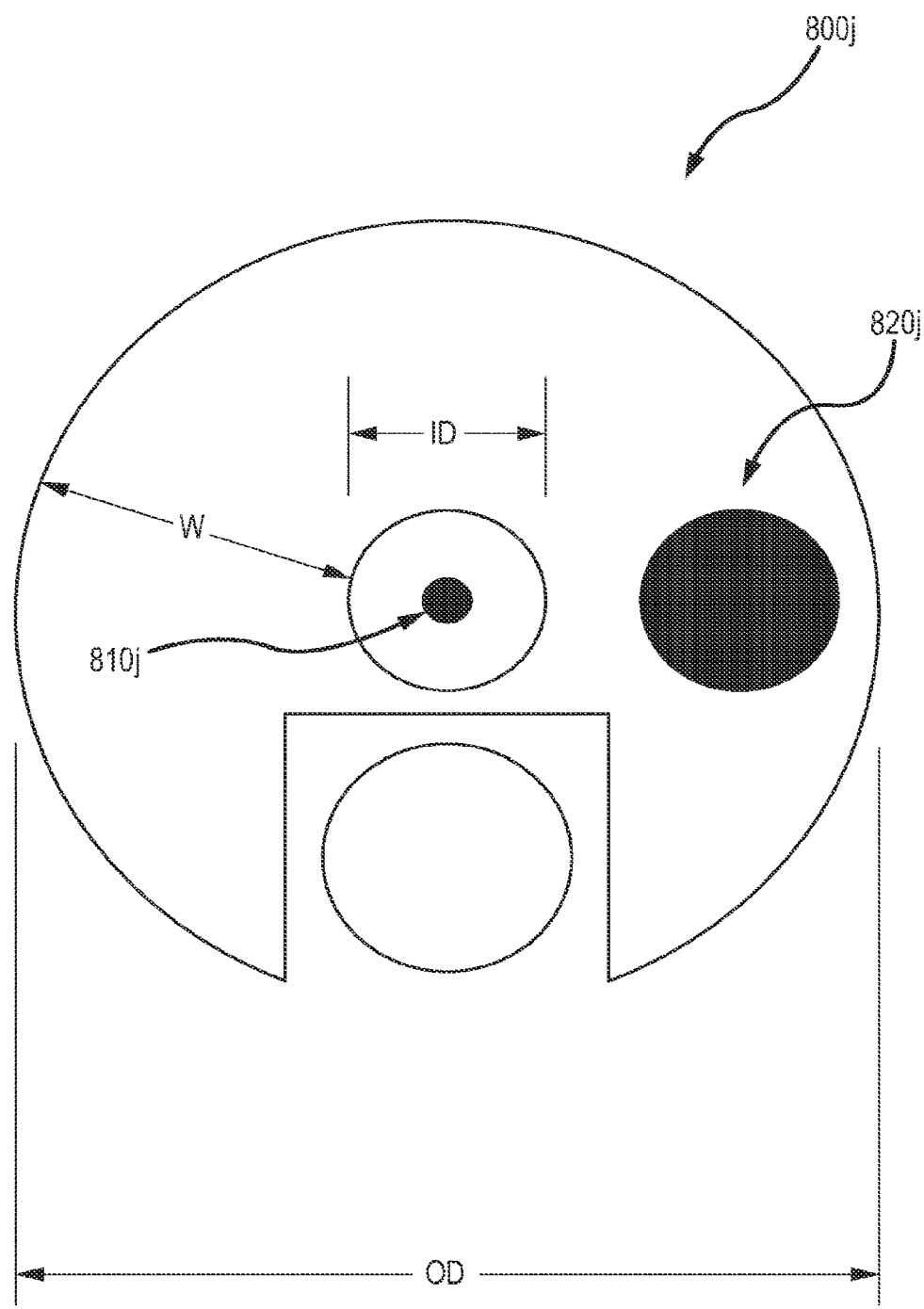

As depicted in FIG. 8J, in some instances a cinchable loop 800j may include a soft, flexible tube having an inner diameter (ID) and an outer diameter (OD). In use, the cinchable loop rotates about a central longitudinal axis 810j of the loop. According to some embodiments, the OD is about 3/16 inch, and the ID is about 1/16 inch. Other suitable dimensions can be used for the tube configuration. In some cases, a cinchable loop may include a longitudinally extending rod or support member 820j within the wall W of the tube, to help enhance torqueability of the loop. The rod or support member 820j can be flexible and stiff, and optionally may be glued in place within the tube wall. The rod or support member 820j can be bendable, yet stiff so as to import additional torqueability to the tube. In some cases, the rod or support member may be placed within a longitudinally extending lumen or slit of the tube. In some cases, a cinchable loop may include a spring or helical member disposed within a wall of the tube, such that the spring or helical member helps the tube resist compressive forces, yet also imports torqueability to the tube while maintaining the bendability of the tube. As depicted here, the OD of the tube may be selected such that upon cinching of the cinchable loop, the loop or tube does not sever or otherwise compromise the patient tissue against which it is moved or compressed. Alternately, the loop, either in a tube or rod form, may have incorporated within its wall or against its ID additional structure such as a tubular braid or helical coils of polymer or metal that enhance torque transmission, without significant wind-up, and reduce kinking.

Figure 9A:
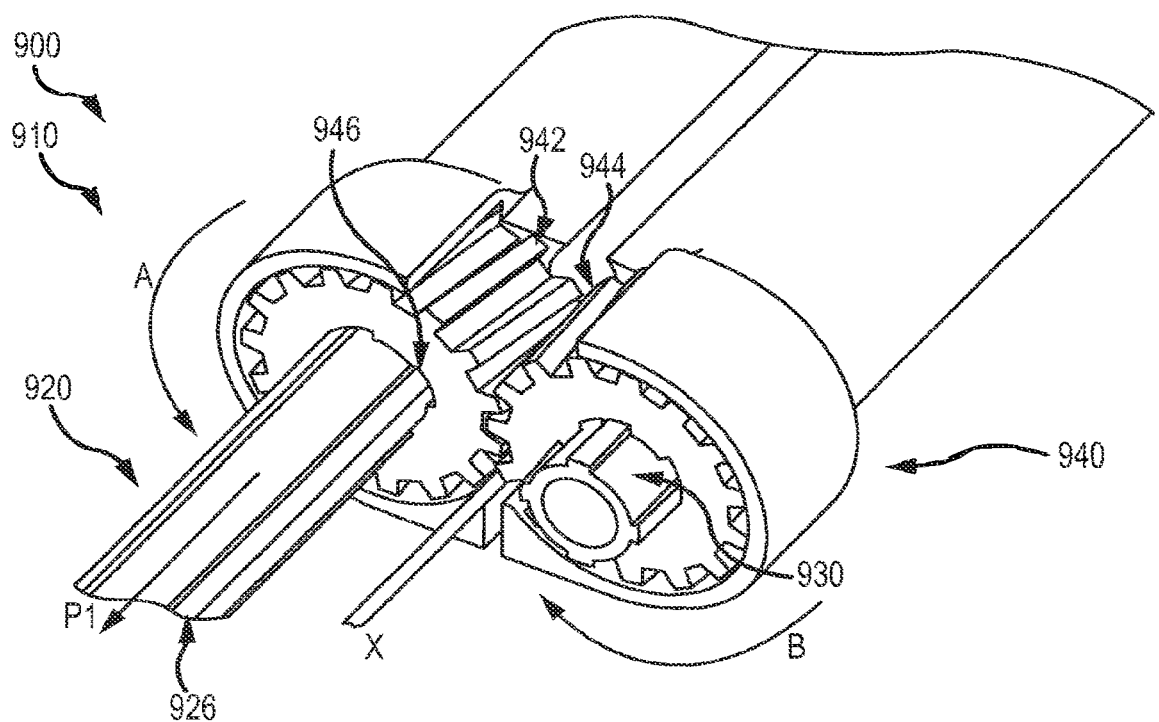
FIGS. 9A, 9B, and 9C depict features of ligature delivery systems and methods according to embodiments of the present invention.
Figure 9B:
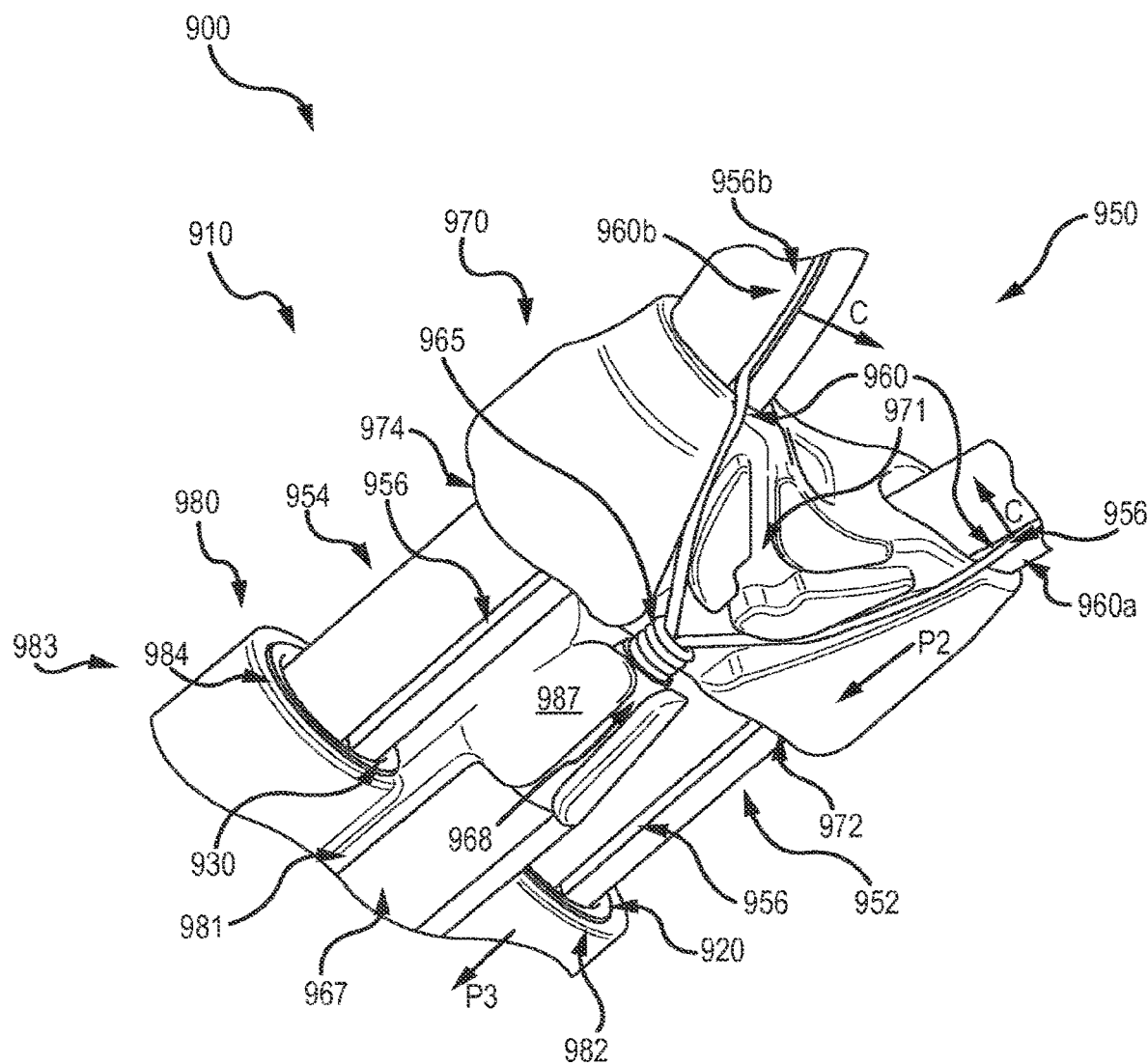
Figure 9C:
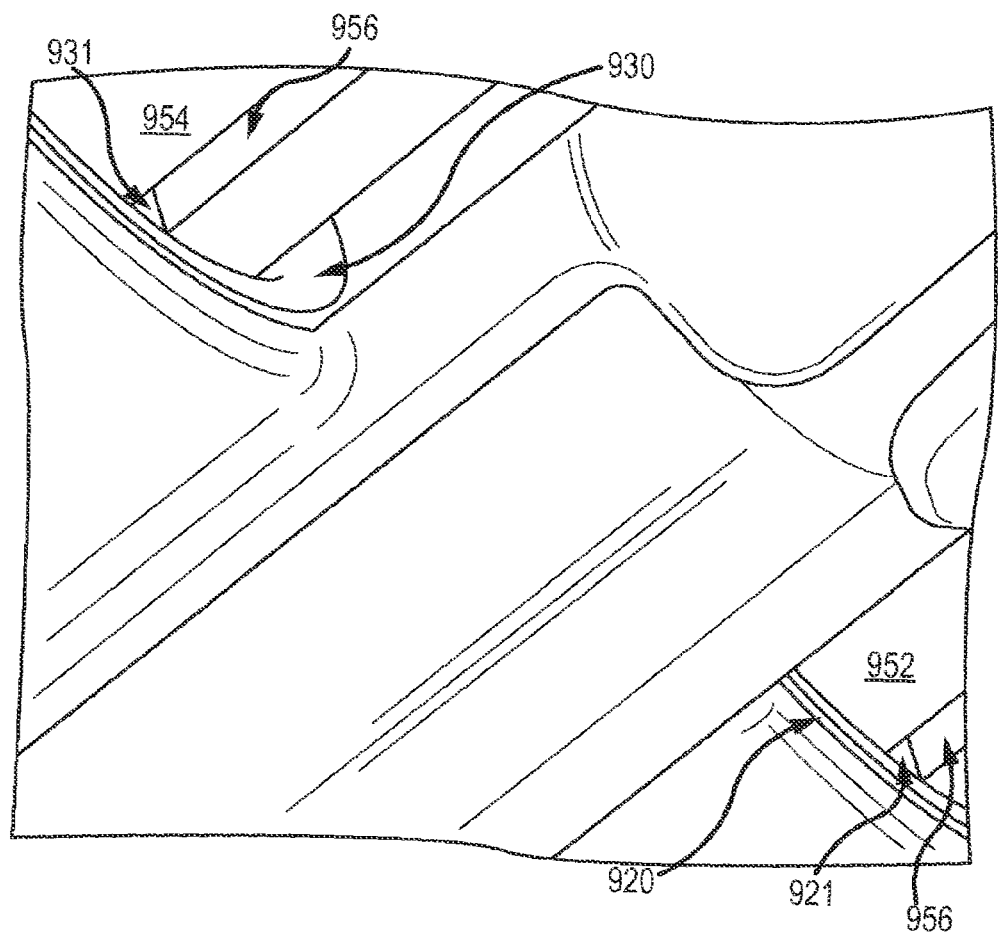

FIGS. 9A and 9B depict additional details of a ligature delivery system, and how actuation of a delivery control mechanism can operate to convert a thread delivery mechanism from a first configuration where a ligature thread is shielded from the tissue of an ensnared anatomical feature, to a second configuration where the ligature thread can be delivered to the anatomical feature. As shown here, the ligature delivery system 900 includes a delivery control mechanism 910 having a first rotary drive 920 and a second rotary drive 930. The first and second rotary drives are coupled together via a gearbox assembly 940, such that torque applied to one rotary drive is transmitted to the other rotary drive. For example, the first and second rotary drives may be aligned in a parallel or co-linear fashion, each rotating about its own central longitudinal axis, in a direction opposite to the other. According to some embodiments, the gearbox assembly 940 includes a first gear 942 coupled with the first rotary drive 920, and a second gear 944 coupled with the second rotary drive 930. Hence, the gearbox assembly may include a dual-gear or multi-gear mechanism. In some cases, first gear 942 may be integral with or part of the first rotary drive 920, and second gear may be integral with or part of the second rotary drive 930. In some cases, the first rotary drive 920 is axially slidable or translatable relative to first gear 942. In some cases, the second rotary drive 930 is axially slidable or translatable relative to second gear 944. In some cases, the second rotary drive 930 does not translate or move axially along the length of the support mechanism relative to the second gear 944. A distal portion of the first rotary drive 920 is coupled with or rotationally fixed relative to a first portion 952 of a cinchable loop 950, and a distal portion of the second rotary drive 930 is coupled with or rotationally fixed relative to a second portion 954 of the cinchable loop 950. As shown here, the cinchable loop 950 includes a groove or slot 956 that received a suture or ligature thread 960. The cinchable loop first portion 952 may rotate within or relative to a first guide or aperture 972 of a deflector mechanism 970, and the cinchable loop second portion 954 may rotate within or relative to a second guide or aperture 974 of the deflector mechanism 970. As shown in the enlarges perspective view of FIG. 9C, the first rotary drive 920 may include a pin or protrusion 921 that engages or inserts into the thread delivery mechanism slot 956. Similarly, the second rotary drive 930 may include a pin or protrusion 931 that engages or inserts into the thread delivery mechanism slot 956. Such pins, protrusions, tabs, or splines 921, 931 can help to transfer torque from the rotary drives to the thread delivery mechanism when the rotary drives are rotated. In this way, the cinchable loop can be simultaneously torqued or forcibly rotated from two opposing sides of the loop. As described elsewhere herein, the rotary shafts 920, 930 can be used to rotate the suture carrier end portions 952, 954 in opposing directions, so as to position the slot 956 and the suture thread carried by the slot 956 to the desired orientation for depositing the thread loop about the base of the left atrial appendage. Hence, the cinchable loop 950 may operate as a torqueable suture carrier, that can be rolled or rotated so as to deliver a suture or ligature thread to an anatomical site, for example to the left atrial appendage or the base thereof. In some instance, the cinchable loop 950 is constructed of a plastic or similar flexible material. As shown here, a rotary drive may include one or more splines which engage one or more grooves of a gear. For example, rotary drive 920 may include one or more splines 926 which engage one or more grooves 946 of a gear 942. Relatedly, rotary drive 930 and gear 944 may include similar corresponding features.

In use, a physician or operator can actuate a knob or other aspect of the system so as to rotate the first rotary drive 920 in a first direction (e.g. as indicated by the counter-clockwise arrow A), which in turn rotates the second rotary drive 930 in a second direction (e.g. as indicated by the clockwise arrow B). In this way, the groove or slot portions 956a, 956b (and corresponding ligature thread portions 960a, 960b) can turn toward one another, as indicated by arrows C. Similar turning motions are illustrated by the system configuration transition from FIG. 8A to FIG. 8B, and by the system configuration transition from FIG. 8C to 8D. In this way, a delivery control mechanism that includes a first rotary drive coupled with a first section 810a of a cinchable loop 810 and a second rotary drive coupled with a second section 810b of the cinchable loop, can be actuated such that rotation of the first rotary drive drives counter-rotation of the second rotary drive and the rotating drives coordinate to switch the cinchable loop from a first configuration (e.g. FIGS. 8A, 8C) to a second configuration (e.g. FIGS. 8B, 8D). When in the second configuration, tension in the suture may facilitate unloading of the suture loop 820 from the carrier groove 830. When the thread loop has been delivered to the anatomical site, the operator may then remove the proximal tail thread from the translating knob, or clip the proximal tail portion at location X as indicated in FIG. 9A, so that the ligature delivery system, optionally along with the suture carrier tube, may be withdrawn or removed from the patient.

Accordingly, a delivery control mechanism 150 such as that depicted in FIG. 1 can effect coordinated axial rotation between a first end portion 113 of the delivery mechanism 110 and a second end portion 114 of the delivery mechanism 110, where the first and second end portions 113, 114 bound a central or distal portion 115 of the cinchable loop 112. Hence, with returning reference to FIGS. 9A and 9B, in some embodiments a delivery control mechanism may include a gearbox assembly 940 in operative association with the first end portion 952 and the second end portion 954, such that the gearbox assembly effects coordinated axial rotation of the first end portion 952 and the second end portion 954. Further, as depicted here, the first rotary drive 920 can be coupled with the first section 952 of the cinchable loop and the second rotary drive 930 can be coupled with the second section 954 of the cinchable loop, such that applied torque is transmitted between the first and second rotary drives to rotate the torqueable cinchable loop 950. In this way, a torque or twisting or rotating force applied to one rotary drive is transmitted to the other rotary drive, and the combined rotating action of the rotary drives operates to rotate the cinchable loop, or that portion of the thread delivery mechanism bounded by the first and second rotary drives. In some cases, the support mechanism 980 has an engagement assembly 981, such as a slot, a recess, a groove, or a clamp, that receives or engages the carrier 967 of the ligature assembly. In some cases, the support mechanism 980 has an engagement assembly 983 that includes a first aperture or guide 982 and a second aperture or guide 984. For example, the engagement assembly 983 may include a first lumen or channel 982 and a second lumen or channel 984, such that a first rotary drive 920 can be disposed within the first channel 982 and coupled with the first section 952 of the cinchable loop, and the second rotary drive 930 can be disposed within the second channel 984 and coupled with the second section 954 of the cinchable loop, where the first rotary drive 920 is rotatable and translatable within the first channel or guide 982 and the second rotary drive 930 is rotatable within the second channel or guide 984.

With regard to the process of sizing the ligature loop to the anatomical feature, it can be seen that the first portion 952 of the cinchable loop is slidably received within or along a first aperture or guide 972 of the deflector mechanism 970, and the first portion 952 is also slidably received (together with the first rotary drive 920) within or along a first aperture or guide 982 of the support mechanism 980. Hence, when first rotary drive 920 is retracted proximally as indicated by arrow P1, the first portion 952 of the cinchable loop is similarly retracted proximally through or along aperture or guide 972 as indicated by arrow P2, and also proximally through or along the first aperture or guide 982 (together with the first rotary drive 920) as indicated by arrow P3. Second rotary drive 930 may rotate within or relative to a second aperture or guide 984 of the support mechanism. According to some embodiments, however, the second rotary drive 930 may not translate longitudinally, or otherwise remain translationally fixed, relative to the support mechanism. Correspondingly, the second portion 954 of the cinchable loop 960 may remain fixed translationally relative to a second aperture or guide 974 of the deflector mechanism 970, yet may be able to rotate within or relative to the aperture or guide 974. When the first rotary drive 920 is retracted proximally, the first ligature thread portion 960a also can be drawn proximally through or along the deflector mechanism 970, through the ligature knot 965, and through the ligature thread carrier tube 967. A conical pocket or tab assembly 987 of the support mechanism 980 can hold or receive a distal section of the ligature assembly carrier tube 967. The pocket can be shaped or sized so as to accommodate any of a variety of shapes and sizes of carrier tubes. In some instances, the pocket 987 can be used to locate the carrier tube when the ligature assembly is loaded into the ligature delivery system. The pocket 987 can also be used to temporarily attach the carrier tube 967 to the ligature delivery system. The pocket 987 can also include a slot or aperture through which the ligature thread can be passed when loading the ligature assembly onto the ligature delivery system.

Although the rotary drives are generally shown as linear in shape, it is understood that embodiments of the present invention encompass curved or flexible rotary drives as well. For example, first and second rotary drives 920, 930 may be constructed of a braided tube that can flex or bend about its central longitudinal axis. Relatedly, a support mechanism may be curved or have curved lumens or channels 982, 984 in which such flexible rotary drives may rotate. Although the default orientation of the cinchable loop and deflector mechanism is often shown to have a zero degree yaw deflection with regard to the support mechanism, it is also understood that the deflector mechanism may be constructed to provide an offset relative to the support mechanism (e.g. 45 to 90 degrees yaw) when in a default or unactivated configuration.

Use with Alternative Ligature Assemblies

In the embodiments depicted in FIGS. 9A and 9B, the ligature assembly includes a carrier tube 967, and a ligature thread having a proximal tail 964, a knot 965, and a distal loop portion 960a, 960b. As shown in FIG. 9B, a distal section 968 of the carrier tube 967 can be used to providing an opposing force against the knot 965 when a translating portion 960a of the thread is pulled proximally through the knot 965. In some instances, however, a ligature assembly may not include a carrier tube or knot pusher. For example, with reference to FIGS. 2A and 2B, a ligature assembly may include a knotted ligature thread having a proximal tail and a distal loop, and no carrier tube or pusher. In some cases, with reference to FIG. 2C, a ligature assembly may include a proximal tail portion, and a distal portion which can be formed into a loop by passing the proximal portion through a ratchet mechanism. Hence, embodiments of the present invention encompass systems that provide a means for providing an opposing force against a knot or ratchet mechanism, for example in cases where a ligature assembly does not include a carrier tube or knot or ratchet pusher. As depicted in FIG. 9B, the deflector mechanism 970 may include a pocket or stop 971 that receives a ligature assembly knot or ratchet, and the pocket or stop 971 can be used to provide an opposing force when drawing the translating portion 960a of the ligature thread or device through the knot or ratchet mechanism, so as to cinch or reduce the diameter of the ligature loop. It is understood that such a pocket or stop can also be placed at any suitable location on the support mechanism 980, for example at or near the location where tabs or conical pocket 987 are used to hold a distal portion of the carrier tube 967.

Additional Features of System Operation

Figure 10B:
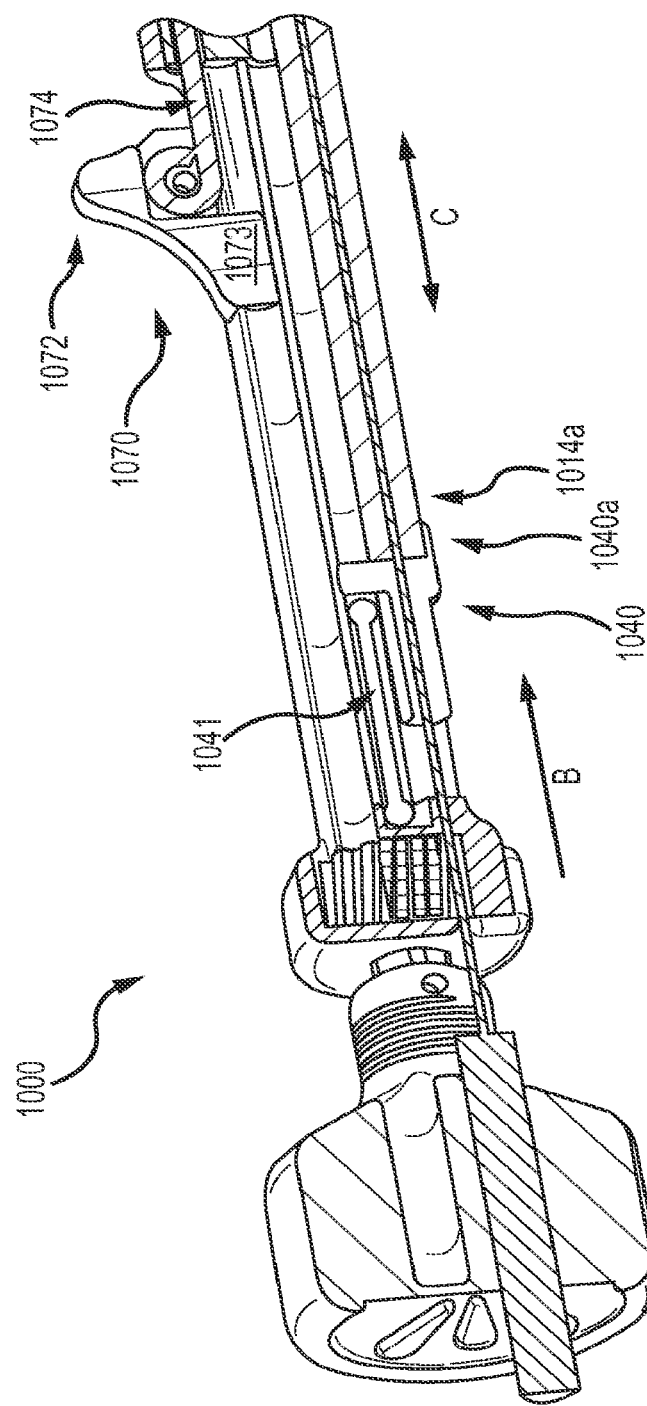

FIGS. 10A and 10B illustrate aspects of a ligature delivery system 1000 for use with a ligature assembly 1010 according to embodiments of the present invention. As shown here, the ligature assembly 1010 includes a carrier tube 1012 having a main body 1014, and a frangible portion 1016 which has been detached from the main body 1014. The frangible portion 1016 is fixed with a proximal tail portion 1018 of the ligature thread. In addition to, or as an alternative to, the pin and groove features depicted in FIG. 3B for example, a rotatable and translatable knob 1022 of a delivery control mechanism 1020 may include a channel or pocket 1024 that releasably coupled with the frangible portion 1016. Hence, when the knob is retracted proximally, or translated axially, relative to the support mechanism or handle 1030 as indicated by arrow A, the frangible portion 1016 is also drawn proximally in the direction indicated by arrow A. Accordingly, cinching of the thread delivery mechanism loop is coincident with cinching of the ligature thread loop. In some instances, the frangible portion or break-off pull handle 1016 attached with the proximal tail end of the suture can be wedged into the groove 1024 of the rotary knob 1022, so as to keep axial movement of the suture carrier loop the same as that of the suture thread itself.

Figure 10C:
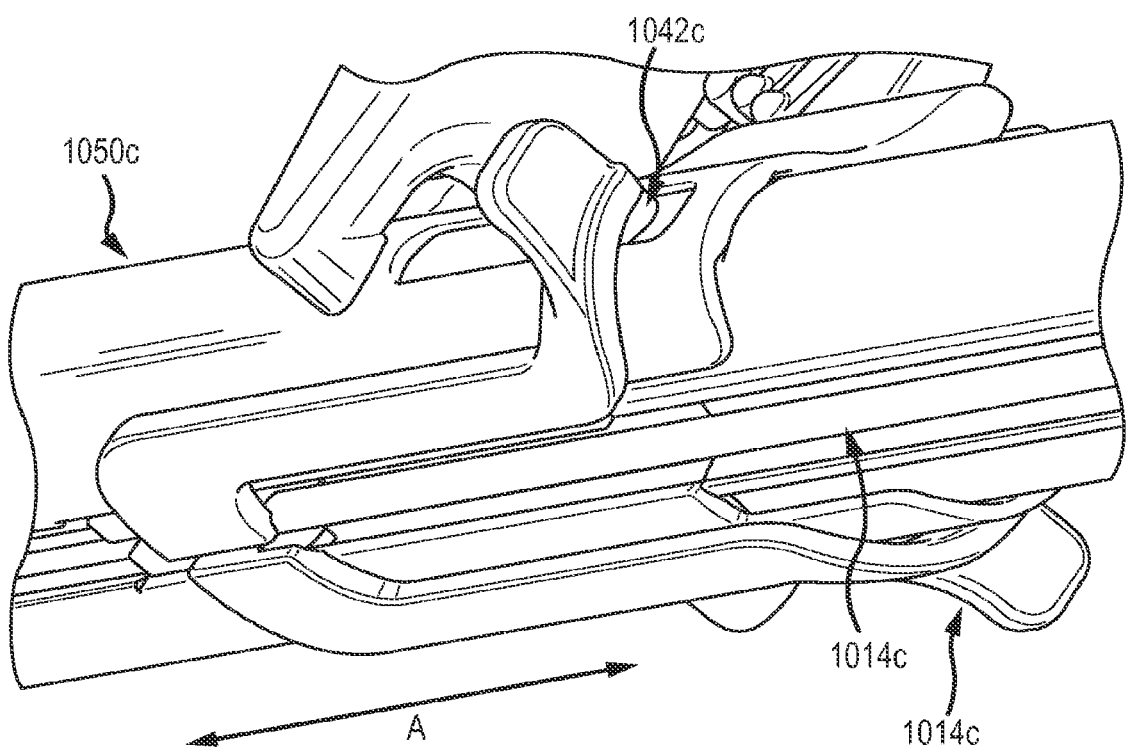

The ligature delivery system 1000 may also include a spring loaded or biased catch mechanism 1040, which can be used to hold or secure a proximal portion of the carrier tube main body 1014. For example, the catch 1040 can be biased to press against the main body 1014 in the direction indicated by arrow B. As seen in the cross-section view of FIG. 10B, the ligature delivery system may include a spring or other biasing element 1041 that operates to press or bias the catch 1040 toward a distal direction as indicated by arrow B. In this way, the catch mechanism 1040, in combination with the recess 981 and pocket 987 shown in FIG. 9B, can releasably secure or engage the carrier tube of the ligature assembly with the support mechanism. The catch mechanism 1040 can include an aperture or lengthwise slot through which the ligature thread can be passed when loading the ligature assembly onto the ligature delivery system. In some instances, the catch mechanism 1040 may include a lip or edge 1040*a* that helps secure a proximal section 1014*a* of the carrier tube in place, relative to the support mechanism. Similarly, as shown here, the handle or support mechanism 1050 may include a lengthwise slot through which the ligature thread can be passed when loading the ligature assembly onto the ligature delivery system. FIGS. 10A and 10B also illustrate that a ligature delivery system can include a deflection control mechanism 1070 having an actuation assembly 1072 and a linkage assembly 1074 coupled with a deflector mechanism (not shown). The actuation assembly 1072 shown here includes a sliding or thumb-actuated button or lever 1073 that can be translated relative to the support mechanism distally or proximally as indicated by arrow C. As seen in the embodiment depicted by FIG. 10C, the catch 1040*c* may include tabs, prongs, or guides 1042*c* for engaging the support mechanism or handle 1050*c*, so as to facilitate relative transitional movement (as indicated by arrow A) between the catch 1040*c* and the support mechanism 1050*c*, when loading or discharging a main body 1014*c* of a ligature assembly. For example, the catch 1040*c* can be drawn proximally when unloading a used carrier tube and re-loading a new ligature assembly, and moved distally once the new ligature assembly is in place, thus securing the main body 1014*c* relative to the support mechanism.

Figure 11:
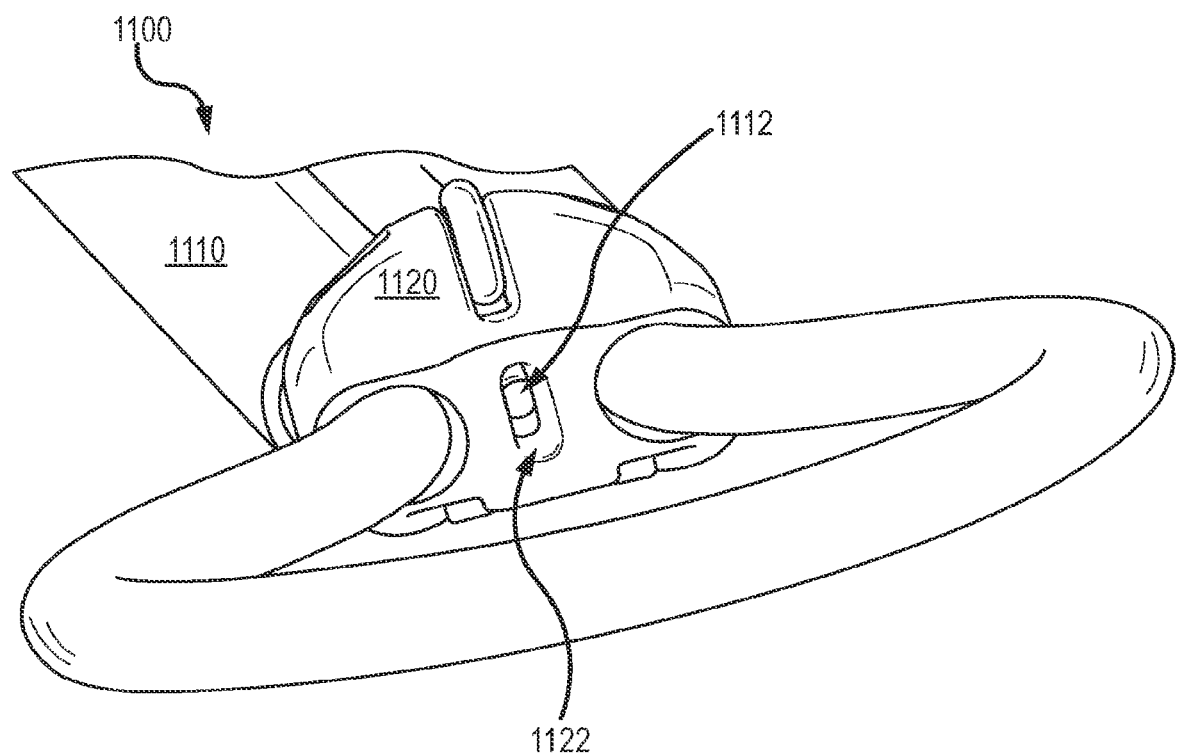
FIG. 11 illustrates aspects of ligature delivery systems and methods according to embodiments of the present invention.

FIG. 11 shows an end distal view of an exemplary ligature delivery system 1100. As depicted here, each of the support mechanism 1110 and the deflector mechanism 1120 may include one or more apertures, channels, or guides for receiving fiber optic light sources or transmission means, imaging or visualization devices or means, irrigation fluid or means, suction devices, grasping devices such as forceps, and the like. For example, support mechanism 1110 may include a longitudinally extending passage or lumen 1112 that houses or receives a fiber optic light transmission assembly. Similarly, deflector mechanism 1120 may include an aperture or passage 1122 that also receives the fiber optic light transmission assembly. In this way, the operator or user can visualize the anatomical environment in which the cinching loop is placed, and the anatomical feature to which the ligature thread is applied. Hence the ligature delivery system may also include or be configured for use with a light source. In some cases, operation of a delivery or applicator system can include the use of an endoscope, with or without protective sheath, or a light wand or LED to enhance visualization. In some cases, a light wand or LED may be integral with a shaft of the delivery or treatment device.

Optionally, the lumens or apertures 1112, 1122 may house or receive an irrigation tube or provide a passage for delivering an irrigation fluid to the surgical area or a desired anatomical structure. Hence the ligature delivery system may also include or be configured for use with an irrigation fluid source.

In some instances, the lumens or apertures 1112, 1122 may house or receive a suction tube or provide a passage for delivering suction or a vacuum to the surgical area or a desired anatomical structure. For example, suction or negative pressure provided via such a feature can operate to secure or grasp an anatomical feature within the patient, so as to grasp a particular anatomical structure or positionally stabilize the ligature delivery system relative to the surgical area. Hence the ligature delivery system may also include or be configured for use with a suction or vacuum source. A suction member can seal or interface with an anatomical feature such as the left atrial appendage, so as to adhere to or grasp the tissue, so that the anatomical feature can be extended or maneuvered as desired, and an occlusive device or ligature thread can be delivered to the anatomical feature. In some instances, the lumens or apertures 1112, 1122 may house or receive a grasping mechanism such as a forceps, which can be used to manipulate various anatomical structures of the patient. For example, a forceps device delivered through the lumens or apertures 1112, 1122, may be used to secure or grasp an anatomical feature within the patient, or to grasp a particular anatomical structure or positionally stabilize the ligature delivery system relative to the surgical area. Hence the ligature delivery system may also include or be configured for use with a grasping mechanism or forceps device. A grasping mechanism or forceps can releasably attach with an anatomical feature such as the left atrial appendage, so as to adhere to or grasp the tissue, so that the anatomical feature can be extended or maneuvered as desired, and an occlusive device or ligature thread can be delivered to the anatomical feature.

In some instances, a suction cone or cup can be extended distally beyond the distal end of the closure delivery means. In this way, the suction means can attach to or engage the LAA. By operating handle mechanisms of the treatment system, the closure delivery means can be advanced distal to the suction means, and can be used to deliver the closure means or ligature to the base of the LAA. The snare or ligature can be tightened about the LAA, and activation of a system trigger can release the suture in place about the LAA.

With returning reference to FIGS. 4A and 4B, a ligature delivery system 400 may include a ligature assembly discharge mechanism 490 operable by a system user to discharge the ligature assembly carrier tube 412*a* from the support mechanism 430. For example, the discharge mechanism 490 may include an ejector 492 coupled with a catch 494 via a linkage 496. In use, the operator may retract the catch 494 proximally, which draws the linkage proximally, which in turn draws the ejector proximally 492, thus forcing the carrier tube 412*a* away from the support mechanism 430. Optionally, the operator may advance the catch 494 distally, thus forcing the distal portion of the carrier tube 412*a* against the wedge shaped ejector 492, such that the distal carrier tube portion slides along the ejector in a ramping fashion, thus expelling the carrier tube. In some instances, the discharge mechanism can be actuated once the delivery system and carrier tube have been withdrawn from the patient, following application of a cinched ligature loop. In some instances, a ligature delivery system may not include such a discharge mechanism, and a surgeon or operator may simply remove the carrier tube from the support mechanism by grasping the carrier tube and retracting the carrier tube from the engagement mechanism or channel in which the carrier tube was loaded.

As depicted in FIG. 12, a ligature delivery system 1200 can be used in conjunction with a tissue grasping or engagement mechanism 1250. Hence, a surgeon or operator can perform discrete operations with two different devices. That is, the tissue engagement mechanism 1250 can be used to grasp, maneuver, hold, or position the patient anatomy (e.g. left atrial appendage) as desired, and the ligature delivery system 1200 can be used to deliver a ligature loop or closure means to the patient anatomy. Hence, according to one embodiment, a surgical procedure may include approaching the patient anatomy or left atrial appendage with the engagement mechanism 1250, and fixing the engagement mechanism to the patient tissue. For example, the procedure may include applying a suction or vacuum through an elongate tubular member 1252 and the suction cup or cone 1254, so that the suction cup 1254 securely seals with the patient anatomy. The elongate tubular member and/or suction cup may be bendable, rotatable, and flexible as needed for any particular application. In a left atrial appendage procedure, the surgeon or operator can draw a portion of the LAA into the suction cup 1254 and maneuver the engagement mechanism 1250 so as to expose the base of the LAA. While holding the LAA in place with the engagement mechanism 1250, the surgeon can then advance the cinchable loop 1210 of the ligature delivery system distally along the elongate tubular member 1252 as indicated by arrow A, and over the suction cup 1254. Hence, instead of maneuvering the cinchable loop directly over the patient anatomical structure as described elsewhere herein the surgeon or operator can maneuver the cinchable loop over the engagement mechanism (which is already in contact with the patient structure). In some instances, the engagement mechanism 1250 and the ligature delivery assembly 1200 may be inserted into the patient via different or separate access locations or ports (e.g. engagement mechanism via a sternotomy, and ligature delivery assembly via a thoracotomy). In some instances, the engagement mechanism 1250 and the ligature delivery assembly 1200 may be inserted into the patient via a common access location or port. In some cases, the engagement mechanism and delivery assembly may be used during an open-heart procedure.

As shown here, the suction cup 1254 may include a rim or circumferential sealing portion 1255 that can be used to engage the base or the left atrial appendage. With the suction cup 1254 engaged with the left atrial appendage, and the cinchable loop 1210 disposed about the suction cup 1254, the surgeon or operator can cinch the loop 1210, optionally while sliding the loop further distally along the cup, or rolling the loop distally over the surface of the cup. In some instances, the shape of the suction cup can help to deliver the cinchable loop 1210 to the base of the left atrial appendage. For example, the suction cup may have a distally tapering portion 1256, such that when the cinchable loop is tightened against or rolled along the suction cup, and advanced distal to the equator of the cup, the cinchable loop is guided toward the desired anatomical target (e.g. base of the left atrial appendage). In some instances, the materials of the cinchable loop and suction cup may be configured to provide traction therebetween, which can facilitate rolling of the cinchable loop against the outer surface of the suction cup. For example, either or both of the cinchable loop and suction cup may include a rubbery outer material or textured surface. Once the cinchable loop has been placed about the left atrial appendage, cinched as desired, and rotated so as to orient the suture thread loop to the delivery position, the suture thread loop can be unloaded from the cinchable loop and delivered to the patient tissue. For example, the suture loop can be applied to the patient tissue at or near where the rim or circumferential sealing portion 1255 engages the patient tissue.

In some instances, the shape and size of the suction cup 1254 may be configured specifically for use with a particular anatomical structure of the patient. For example, the shape and size of the suction cup may be configured for engagement with the left atrial appendage of a patient. In some instances, the rim 1255 is curved, and presents a laterally compressed, truncated cone shape. The rim 1255 can be shaped and sized to match the surface of the heart or the base of the left atrial appendage. In some instances, a suction cup 1254 may present an elongate trumpet shape, that can be easily collapsible, compressed into a small shape, and delivered through an access port (e.g. 12 mm port), and then opened into the trumpet shape after insertion into the patient. When drawing the left atrial appendage into an elongate trumpet-shaped suction device, the trumpet-shaped device can operate to squeeze blood out of the left atrial appendage as the left atrial appendage is compressed by the trumpet-shaped suction cone. As depicted in the wider configuration of FIG. 12, when drawing the left atrial appendage into the suction cup 1254, the bulb-shaped or prolate suction device draws the left atrial appendage in, and operates to expand the left atrial appendage. In this way, blood is not forced out of the left atrial appendage, but rather remains in the left atrial appendage. Once the left atrial appendage is cinched, the trapped blood therein may eventually form a clot and be absorbed within the body with no adverse effect. Accordingly, the suction cup 1254 is sufficiently strong or rigid to maintain its shape upon application of the suction, and is also sufficiently flexible to be folded or compressed and inserted into a patient via a port or access site (e.g. between the ribs, in a thoracotomy).

In some instances, the engagement mechanism 1250 may include a flexible or rotatable joint or connection 1258 between the elongate tube 1252 and the suction cup 1254. For example, the engagement mechanism 1250 may include a joint or connection similar to that described elsewhere herein with regard to the joint or connection between the support mechanism and the deflector mechanism of the ligature delivery assembly. In some cases, the joint or connection may include a ball joint or a hinge joint. The engagement mechanism may also include a deflection control mechanism, which operates to actuate the suction cup in pitch and yaw orientations, similar to that described elsewhere herein with regard to the deflection control mechanism of the ligature delivery assembly. In some cases, the deflection control mechanism of the engagement mechanism may include linkages, push-pull rods, and the like, which can rotate or deflect the suction cup as desired, for example so as to angle the suction cup for facile engagement with the left atrial appendage of a patient. Relatedly, such deflection control mechanisms can be used to actuate the joint or connection 1258, or otherwise maneuver suction cup 1254 relative to the elongate tube or handle 1252. In some cases, an engagement mechanism 1250 may be manufactured so as to provide a fixed angle or relative positional relationship between the suction cup 1254 and the elongate tube 1252. In some cases, an engagement mechanism 1250 may be manufactured so as to provide an adjustable angle or relative positional relationship between the suction cup 1254 and the elongate tube 1252. In some cases, an engagement mechanism 1250 may include an elongate tube 1252 having an adjustable length. In some cases, the engagement mechanism 1250 may provide for adjustable pitch of the suction cup 1254 relative to the elongate tube 1252. In some cases, the engagement mechanism 1250 may provide for adjustable yaw of the suction cup 1254 relative to the elongate tube 1252. In some cases, the engagement mechanism 1250 may provide for both adjustable pitch and adjustable yaw of the suction cup 1254 relative to the elongate tube 1252. In some cases, the engagement mechanism 1250 may provide for adjustable pitch, adjustable yaw, adjustable roll, or any combination thereof, of the suction cup 1254 relative to the elongate tube 1252.

In some instances, the engagement mechanism 1250 may be used, without assistance from the ligature delivery assembly 1200, to deliver a ligature loop or closure means to a patient tissue. For example, a surgeon or operator can place a distal portion of a ligature assembly carrier tube at a stop or tab 1262 of the suction cup 1254. The stop or tab 1262 may include a slot 1264 and an aperture or conical pocket 1266 which receive the ligature thread, and the ligature loop can be wrapped about a groove, recess, or other thread engagement feature 1268 that is disposed about the cup rim or margin 1255. Hence, the distal tip of the carrier tube can be inserted into or engaged with the conical pocket 1266. With the distal tip of the snare or carrier tube (not shown) engaged with the stop or tab 1262, and the suture thread loop (not shown) wrapped about the suction cup so as to engage the groove 1268, the suction cup 1254 can be placed into position relative to the patient anatomical feature (e.g. about the base of the left atrial appendage), optionally with applied suction to secure the anatomical feature to the suction cup, and the suture can be tightened so as to more closely approximate the anatomical feature. In this way, the presence of the suction cup can help to shield or protect the patient tissue from the suture thread as the thread is cinched about the patient tissue. For example, any slicing or cutting effect the cinching suture may otherwise have on the patient tissue is avoid, due to the presence of the suction cup which is disposed between the thread and the tissue. When the suture is placed and tightened as desired, the surgeon or operator can roll or unload the suture loop from the groove 1268, over the cup rim 1255, and onto the patient tissue. Optionally, the surgeon or operator may thereafter further cinch the suture, remove the distal carrier tube portion from the stop or tab 1262, withdraw the engagement mechanism, withdraw the carrier tube, and/or sever the suture thread, for example as describe elsewhere herein. In some instances, the engagement mechanism 1250 and the ligature assembly may be inserted into the patient via different or separate access locations or ports (e.g. engagement mechanism via a sternotomy, and ligature assembly via a thoracotomy). In some instances, the engagement mechanism 1250 and the ligature assembly may be inserted into the patient via a common access location or port. In some cases, the engagement mechanism and ligature assembly may be used during an open-heart procedure. In some instances, cinching of the ligature thread loop and contraction of the suction cup, optionally due at least in part to suction applied through the elongate tube, can be performed in a coordinated fashion.

In use, the shaft 1252 can be approximated to the LAA, and the suction means 1254 is used to grasp the LAA. The closure delivery means 1200 can be used to slide or advance a looped ligature over or along the suction means 1254 in a proximal direction, and to further slide or advance the looped ligature over the LAA. In this way, the shaft 1252 and suction means 1254 can be used as a guide for approximating the closure delivery means 1200 toward the LAA, for example to deliver an epicardial occlusion device or closure means. The shaft 1252 and suction means 1254 allows the operator to gain traction relative to LAA, in order to place the closure means on the LAA. When the ligature or closure means is situated as desired, for example about the base of the LAA, the closure means can be actuated or cinched, thereby applying a squeezing or circumferential compression force to the LAA, and optionally tied in place so that it remains about the LAA. Any of a variety of closure means may be used, including cinching ligatures, clips, clamps, sutures, or combinations thereof. The treatment systems disclosed herein are well suited for safely, effectively, and efficiently delivering closure means to the LAA, while minimizing the risk of tearing the LAA or forming only a partial or incomplete closure of the LAA which may lead to undesirable blood clot formation within and release from the LAA.

According to some embodiments, the leading edge or portion of the suction member or suction cup 1254 may house or attach with portions of a ligature or closure means. For example, a ligature loop may be circumferentially associated with a distal portion of the suction means. Optionally, a distal portion of the suction means may include a tube or channeled portions which hold the looped closure means. The tube may include an annular tube ring, for example, having an inner channel which receives the suture. Such tubing or distal portion can be used to deliver the suture as desired.

In some cases, treatment systems can be used to deliver a closure means during an open surgical procedure. In some cases, treatment systems can be used in conjunction with ports to deliver a closure means during a minimally invasive surgical procedure.

In some cases, a suction member may be configured with a rigid tube which acts as a guiding rail to pass the occlusive member over, for example in the case of a lasso or band type device. Relatedly, the rigid tube can acts as a guiding rail to pass the occlusive member along, for example in the case of a clip type device.

According to some embodiments, a suction member or grasping device and an applicator mechanism or suture carrier can provide opposing forces to allow delivery of the occlusive device at the base of the appendage orifice. An applicator system can be guided along the suction member rail and can be activated by an activation mechanism to deliver the occlusive device.

In some instances, an exemplary treatment system can include a shaft with a distal portion and proximal portion. The system can include a suction means, such as a suction cup, for attaching with or grasping the left atrial appendage. The system can also include a closure delivery means which can be used to deliver or apply a closure means, such as a ligature, ratchet lock, crimp, or slip knot, to the base of the LAA thereby occluding or closing the LAA, or segregating the LAA from the left atrium. In some instances, an exemplary treatment system may also include a scope accessory or other visualization mechanism. In some case, the visualization mechanism is separate from the closure delivery means or shaft. In some cases, the visualization mechanism is integral with the closure delivery means or shaft. In some cases, the shaft, suction means, and closure delivery means may be integrated in a single apparatus, which optionally may also incorporate a visualization means. In some instances, the suction means can present a flared or funnel-shaped distal portion, such as a suction cup or element, that interfaces and receives or adheres to a portion of the LAA.

In some cases, the deflection control mechanism, support mechanism, shaft, or other element of the system may include a linkage system that causes the rotation of the suction cup to be about a virtual pivot point (VPP) that may be on or close to the plane of the left atrial base, or any other point away from actual mechanism in order to optimize the movement of the engagement system in the tight confines of surgery. For example, as depicted in FIGS. 12A-1, 12A-2, and 12A-3, a ligature delivery system or tissue engagement mechanism 1250*a* can be used to grasp, maneuver, hold, or position the patient anatomy (e.g. left atrial appendage) as desired, and can also be used to deliver a ligature loop or closure means to the patient anatomy. Hence, according to one embodiment, a surgical procedure may include approaching the patient anatomy or left atrial appendage with the engagement mechanism 1250*a*, and fixing the engagement mechanism to the patient tissue. For example, the procedure may include applying a suction or vacuum through a tubular member 1252*a* and the suction cup or cone 1254*a*, so that the suction cup 1254*a* securely seals or engages with the patient anatomy. As shown here, the engagement mechanism 1250*a* provides a virtual pivot point (VPP) that remains consistent as the engagement mechanism is moved between position 1 (FIG. 12A-1), position 2 (FIG. 12A-2), and position 3 (FIG. 12A-3). In this embodiment, the engagement mechanism includes a non-parallel four bar linkage system 1260*a*, where a handle 1270*a* having a T-shaped distal end provides one link in the linkage system. The links can be provided in various lengths, which can move the virtual pivot point (VPP) along the dashed line or axis 1280*a* to a desired point.

Figure 13A:
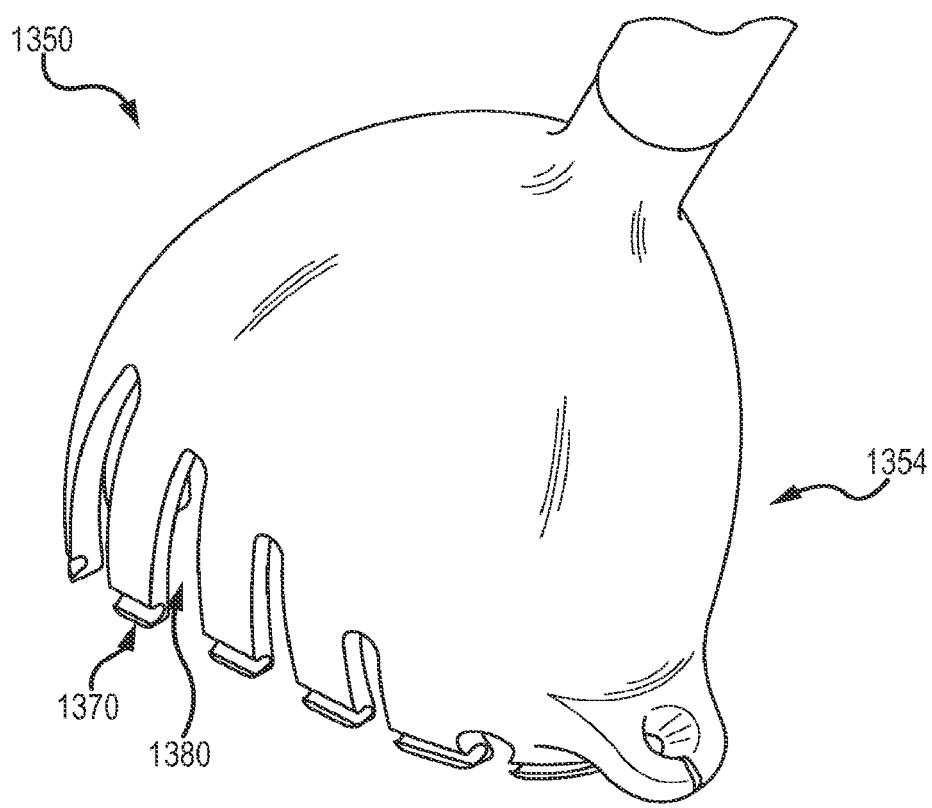
FIGS. 13A and 13B illustrate features of ligature delivery systems and methods according to embodiments of the present invention.
Figure 13B:
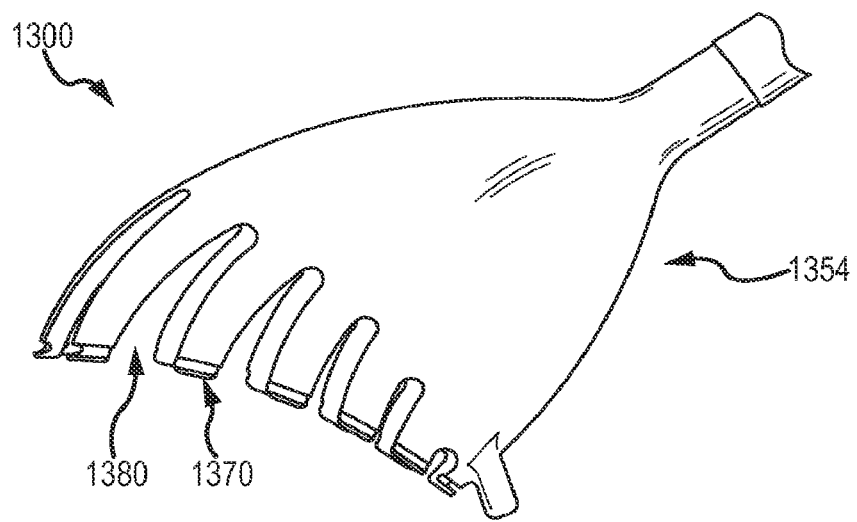

FIGS. 13A and 13B illustrate another embodiment of an engagement mechanism 1350 for use with a ligature assembly, optionally in conjunction with a ligature delivery assembly. As shown here, the engagement mechanism includes a suction cup 1354 having a plurality of fingers or elongate extensions 1370. The suction cup 1354 may also include a very thin membrane (not shown) similar in consistency to that of a surgical glove, which covers the spacings 1380 between the fingers 1370. In this way, the suction cup 1354 can provide an enhanced degree of flexibility between the fingers, and can also provide uninterrupted suction to an anatomical feature to which the suction cup is applied. The fingers 1370 can provide a degree of structural rigidity to the suction cup (relative to the membrane covering the spacings 1380, so as to maintain the overall shape of the suction cup, and the fingers 1370 can also fold or bend in a controlled manner upon application of suction and/or tightening of the suture loop. In use, tightening of the suture or ligature thread can operate to close the flexible fingers toward each other. In some instances, the distal tips of the fingers can touch together, or almost touch together, when the suction cup is contracted or constricted (e.g. due to the suction applied and/or cinching of the thread). The overall shape of the suction cup 1354 can be provided as a trumpet-shape, a football or prolate-shape, or any other desired shape, including a shape that may be shorter in height than in width or length that is not designed to withdraw the appendage within but rather to suck onto the external surface of the appendage for manipulation. In some instances, flexible flaps, which are coupled with the flexible fingers, hold the suture in a looped configuration. The flaps may have distal slotted tube sections which can release the ligature when the flaps are drawn radially inward. Hence, as the suture or ligature is drawn taught, the flaps bend inward, thus allowing the ligature to release through the slots, and situate about the LAA. In operation, an ligature assembly (not shown), optionally in conjunction with a ligature delivery assembly (not shown) can be used with the engagement mechanism 1350 in any of the modalities described elsewhere herein, and in particular according to the techniques discussed above with regard to FIG. 12.

In some instances, an engagement mechanism may include an elongate tube coupled with a suction cup, where the suction cup has a shape configured to interface with an anatomical feature of the patient (including a shape as noted in the preceding paragraph, or as described elsewhere herein). The suction cup may be void of tab, groove, and/or finger features those described herein with regard to FIGS. 12, 13A, and 13B. In use, the suture loop may be advanced over the suction cup and delivered to the anatomical site (e.g. base of left atrial appendage) as desired.

Figure 14:
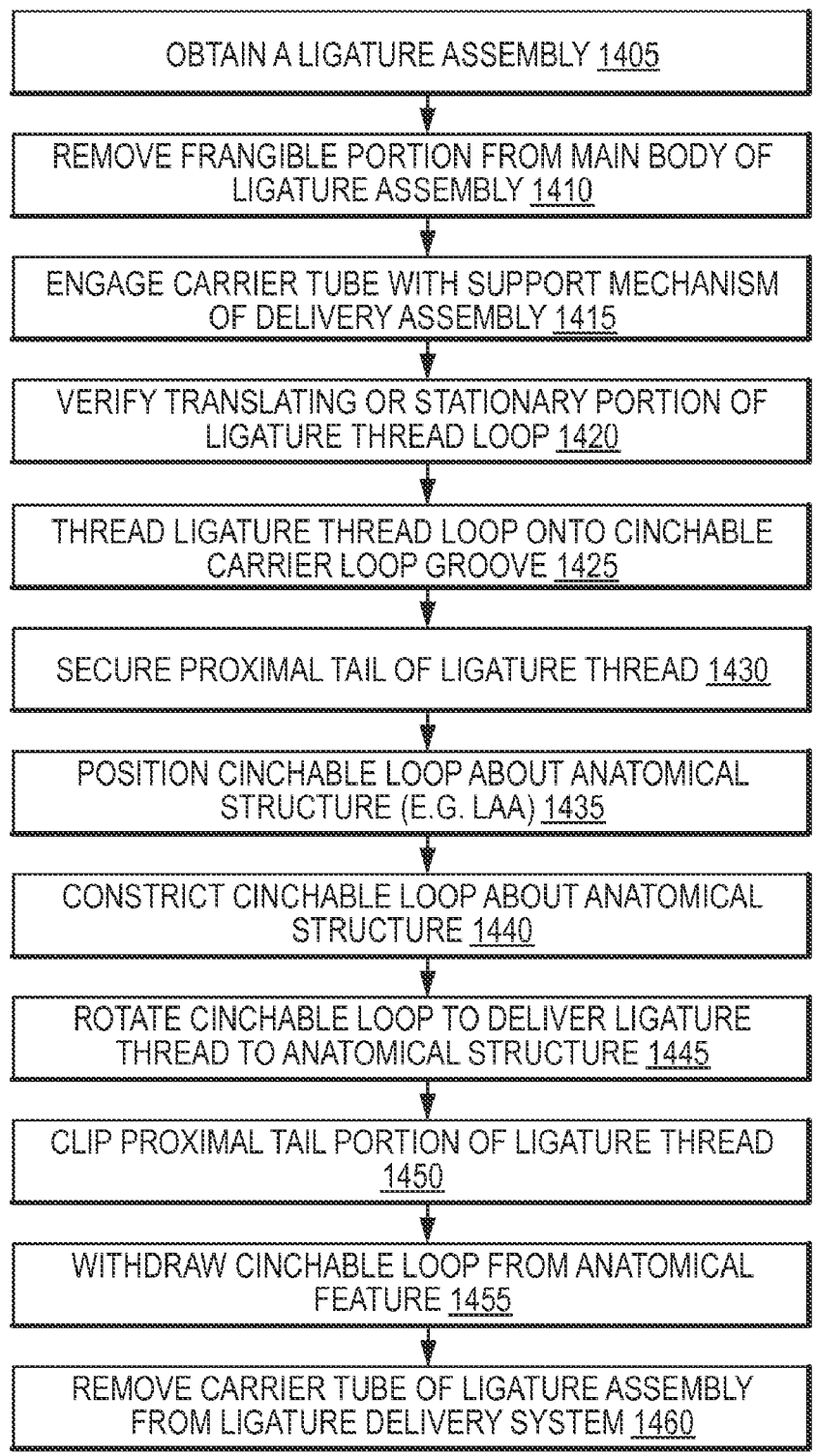
FIG. 14 depicts aspects of ligature delivery methods according to embodiments of the present invention.

FIG. 14 illustrates aspects of an exemplary method according to embodiments of the present invention. Procedure 1400 includes obtaining a ligature assembly or suture device as indicated by step 1405, for example by removing the ligature assembly from a sterile package. In some instances, the ligature assembly may include a ligature suture disposed partially within a tubular body or pusher. The procedure may also include preparing the suture or ligature assembly by removing a frangible portion of the carrier tube or pusher from a main body of the pusher, as indicated by step 1410. In some instances, this step may involve breaking off the proximal pull tab of a carrier tube. Further, the procedure may include loading the carrier tube (e.g. main body) onto a support mechanism of a ligature delivery system as indicated by step 1415. For example, a distal section of the carrier tube main body can be engaged with a distal cone or pocket of the support mechanism, and a proximal section of the carrier tube can be engaged against a spring loaded clip or catch mechanism. The operator or surgeon may also slightly retract a proximal tail of the ligature thread, for example by pulling the frangible portion of the dissociated carrier tube proximally a distance of about one inch, to verify which side of the ligature loop remains stationary and which side is drawn proximally through the loop, as indicated by step 1420. The stationary portion of the ligature thread loop can be inserted into the thread delivery mechanism groove at a location near a non-translating rotary drive, as indicated by step 1425. The ligature thread loop can then be worked around the groove of the cinchable loop carrier of the thread delivery mechanism. A proximal tail of the ligature thread can be fixed relative to a first rotary drive, as indicated by step 1430. For example, the operator may pull the frangible portion of the suture tube to take up slack in the ligature thread, and wedge the frangible portion into a rotary knob slot of a delivery control mechanism. Additionally, the procedure may include inserting the distal portion of the system into a patient's body, or advancing the distal portion to a desired anatomical location of the patient, adjusting the pitch, yaw, or both of the cinchable loop, and positioning the cinchable loop about an anatomical feature of the patient, such as the left atrial appendage (LAA), as indicated by step 1435. The operator may pull or retract the rotary knob or first rotary drive, so as to tighten or cinch the cinchable loop as indicated by step 1440. Further, as indicated by step 1445, the operator can turn the rotary knob or otherwise actuate the first rotary drive, so as to deploy the suture thread to the anatomical structure, as indicated by step 1450. With the ligature loop appropriately positioned about the anatomical structure, the operator can grasp or tug on the exposed proximal suture portion, and cut the suture thread, so as to decouple the cinched suture loop that is engaged with the anatomy from the system that has performed the suture delivery and cinching, as indicated by step 1450. Often, prior to this decoupling, the ligature snare and the delivery system are present together or otherwise engaged as a single unit. The operator may also push in or distally advance the rotary knob so as to loosen the cinchable loop from its grip on the anatomical feature, and remove or withdraw the device from the applied suture strand and anatomical structure as indicated by step 1455. At this point, the ligature delivery system along with the carrier tube can be withdrawn from the patient, leaving the suture in place (for example with the ligature loop disposed about the patient's LAA, and the proximal tail of the ligature thread extending out of the patient's body through an access port or other opening). The surgeon or operator can then slide a pair of scissors or other cutting device along the proximal tail thread, in a distal direction toward the cinched loop. When the scissors are near the knot, the surgeon can then clip the thread at a location proximal to the knot, and remove the severed proximal tail and scissors from the patient, thus leaving the cinched and knotted suture loop disposed about the patient anatomical feature as an implanted medical device. As depicted by step 1460, the operator may also remove the suture tube from the support mechanism by sliding a clip or catch proximally relative to the support mechanism, thus discharging the suture carrier tube from the support mechanism. The wedged pull tab or frangible portion may also be removed from the rotary knob. As desired, this procedure can be repeated so as to apply multiple ligature threads to one or more anatomical structures of the patient's body. Hence, the ligature delivery system can be repeatedly reloaded with any desired number of ligature assemblies to deliver any number of cinched loop implants.

Figure 15:
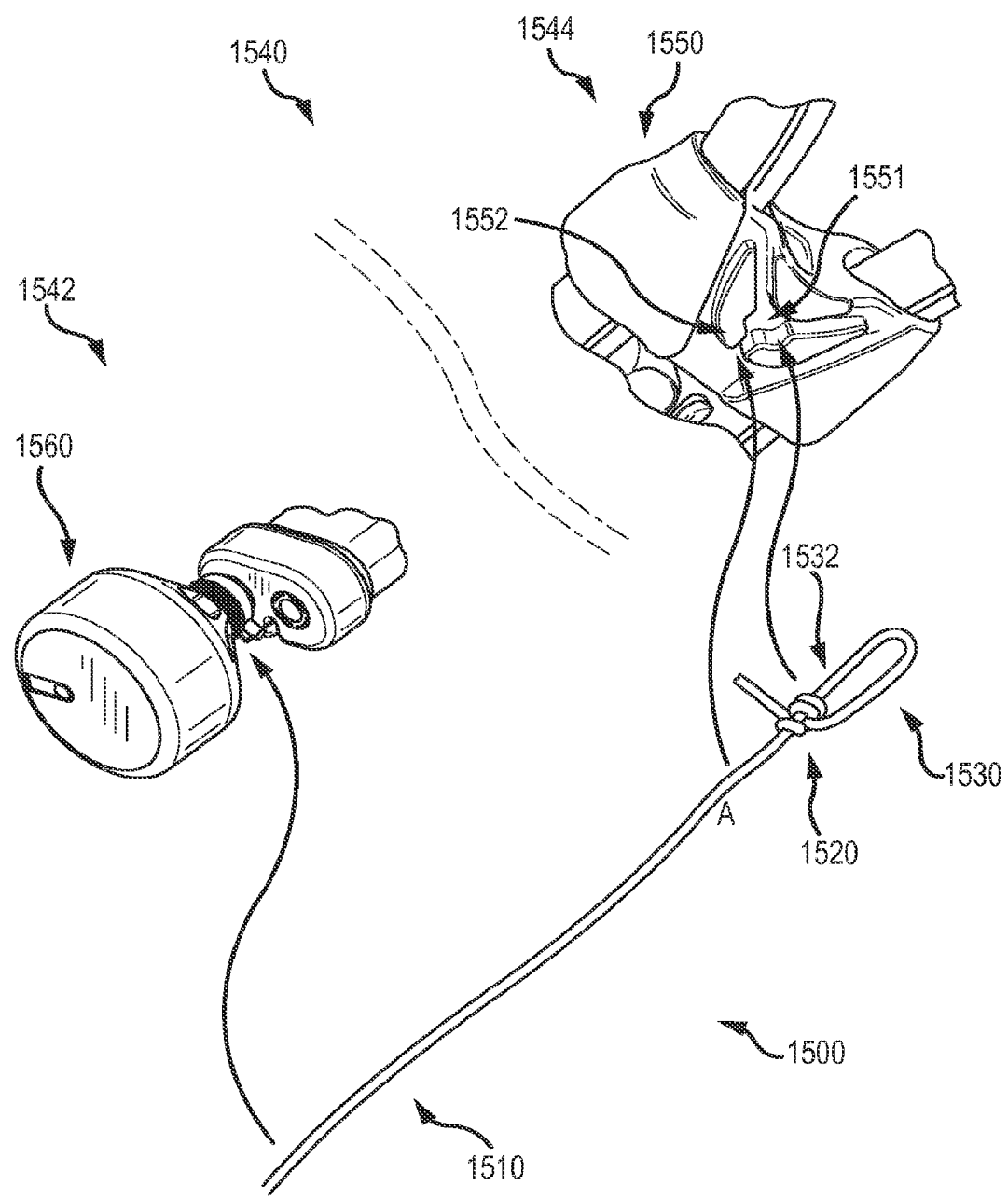
FIG. 15 depicts aspects of ligature delivery systems and methods according to embodiments of the present invention.

As discussed elsewhere herein, in some instances a ligature assembly may include a knotted thread or suture having a distal loop portion and a proximal tail portion, without a carrier or push tube. FIG. 15 illustrates such a ligature assembly 1500 having a proximal tail portion 1510, a one-way knot 1520, and a distal loop 1530. In this broken perspective view of the ligature delivery system 1540, which shows a top view of a proximal portion 1542 of the system and a bottom view of a distal portion 1544 of the system, it can be seen that a support mechanism or deflector mechanism 1550 may include a pocket or stop 1551 that receives the ligature assembly knot 1520. In some instances, the pocket or stop may include a slotted shelf or two protrusions which operate to prevent proximal translation of the knot relative to the support mechanism or deflector mechanism when the tail portion 1510 of the ligature assembly is drawn proximally. Hence, for example, a portion of the thread disposed proximal to the knot, as indicated by location A, can be threaded in the slot 1552 of the pocket. It is understood that such a pocket or stop can also be placed at any suitable location on the support mechanism or on the deflector mechanism. It can also be seen here that the proximal tail portion 1510 of the ligature assembly can be engaged with the ligature delivery assembly, for example by winding the proximal tail portion about a proximal knob 1560, or by fixing the proximal tail portion 1510 relative to a first rotary drive as discussed elsewhere herein. In use, the surgeon or operator can use the cinchable loop of the ligature delivery assembly to place the ligature thread loop 1530 about the anatomical structure, and can use the knob 1560 to draw the thread tail 1510 proximally, so as to cinch the thread loop relative to the patient anatomical structure. Accordingly, the yoke or stop 1551 can be used to provide an opposing force when drawing a translating portion 1532 of the ligature thread proximally through the knot 1520, so as to cinch or reduce the diameter of the ligature loop. In this way, the knot is restrained by the pocket. The translating portion 1532 of the thread passes through the one-way knot 1520 and toward the proximal portion 1542 of the delivery system. In this way, the loop thread can be cinched by applying counter traction via the knob and pocket. The sliding knot operates to secure itself when tightened. Once tightened in place relative to the anatomical structure, the suture thread loop or closure means can be unloaded from the cinchable loop of the ligature delivery device, thus also releasing the knot from the pocket. Thereafter, the suture loop or closure means remains in place about the anatomical structure (e.g. by virtue of the one-way knotted loop). The proximal tail portion 1510 can be released from the knob, and the ligature delivery device can be removed or retracted away from the patient, leaving the suture thread fixed to the patient anatomy. The surgeon or operator can then clip the excess proximal tail portion of the suture thread. In this way, the closure means or ligature loop can be used to tie off the left atrial appendage of a patient, the cecal appendix, or any other desired structure within a patient.

Different arrangements of the components depicted in the drawings or described above, as well as components and steps not shown or described are possible. Similarly, some features and subcombinations are useful and may be employed without reference to other features and subcombinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications can be made without departing from the scope of the claims below.

While exemplary embodiments have been described in some detail, by way of example and for clarity of understanding, those of skill in the art will recognize that a variety of modification, adaptations, and changes may be employed. Hence, the scope of the present invention should be limited solely by the claims.

We claim:

1. A ligature delivery system comprising:
   an anatomical structure closure mechanism;
   a delivery mechanism comprising a cinchable loop that engages the closure mechanism and that rotates between a first configuration whereby the closure mechanism is shielded from an anatomical structure of a patient and encircles the anatomical structure, a second configuration whereby the closure mechanism remains encircled around the anatomical structure and can be released onto the anatomical structure, and a transition configuration between the first configuration and the second configuration, wherein in the transition configuration the closure mechanism remains encircled around the anatomical structure; and
   a delivery control mechanism configured to cinch the cinchable loop about the anatomical structure and that switches the cinchable loop between the first and second configurations.

2. The system according to claim 1, wherein the cinchable loop comprises a groove that engages the closure mechanism when the cinchable loop is in the first configuration.

3. The system according to claim 1, wherein the delivery control mechanism comprises a first rotary drive coupled with a first portion of the cinchable loop and a second rotary drive coupled with a second portion of the cinchable loop.

4. The system according to claim 1, further comprising a support mechanism having a recess configured to receive a proximal tail portion of the closure mechanism.

5. The system according to claim 1, wherein the delivery control mechanism effects coordinated axial rotation between a first end portion of the delivery mechanism and a second end portion of the delivery mechanism, the first and second end portions bounding a central portion of the cinchable loop.

6. A ligature delivery system comprising:
   a delivery mechanism comprising a loop having a loop profile where the loop is adjustable in profile and where the loop engages a closure mechanism between a first configuration and a second configuration, wherein in the first configuration the loop encircles an anatomical structure and shields the anatomical structure from the closure mechanism, wherein in the second configuration the loop remains encircled around the anatomical structure and moves to position the closure mechanism adjacent to the anatomical structure, wherein the loop rotates to move between the first configuration and the second configuration, and a transition configuration between the first configuration and the second configuration, wherein in the transition configuration the closure mechanism remains encircled around the anatomical structure; and a delivery control mechanism that switches the loop between the first and second configurations.

7. The system according to claim 6, wherein the delivery control mechanism comprises a first rotary drive coupled with a first portion of the loop.

8. The system according to claim 7, wherein the delivery control mechanism comprises a second rotary drive coupled with a second portion of the loop.

9. The system according to claim 6, wherein the loop is a cinchable loop.

10. The system according to claim 9 wherein the delivery control mechanism is configured to cinch the cinchable loop about the anatomical structure.

11. The system according to claim 9, wherein the cinchable loop comprises a groove that engages the closure mechanism when the cinchable loop is in the first configuration.

12. The system according to claim 6, further comprising a support mechanism having a recess configured to receive a proximal tail portion of the closure mechanism.

13. The system according to claim 6, wherein the delivery control mechanism effects coordinated axial rotation between a first end portion of the delivery mechanism and a second end portion of the delivery mechanism.

14. A ligature delivery system comprising:
a delivery mechanism comprising a loop, where the loop is configured to be pivotable and adjustable in profile, where the loop engages a closure mechanism and can switch from a first configuration to a second configuration, wherein in the first configuration a portion of the loop houses the closure mechanism in a configuration that shields an anatomical structure from the closure mechanism and encircles the anatomical structure, wherein in the second configuration the loop remains encircled around the anatomical structure and permits release of the closure mechanism onto the anatomical structure, and a transition configuration between the first configuration and the second configuration, wherein in the transition configuration the closure mechanism remains encircled around the anatomical structure; and a delivery control mechanism that switches the loop from the first configuration to the second configuration.

15. The system according to claim 14, wherein the delivery control mechanism is configured to cinch the loop about the anatomical structure.

16. The system according to claim 14, wherein the loop comprises a groove that engages the closure mechanism when the loop is in the first configuration.

17. The system according to claim 14, wherein the delivery control mechanism comprises a first rotary drive coupled with a first portion of the loop.

18. The system according to claim 17, wherein the delivery control mechanism comprises a second rotary drive coupled with a second portion of the loop.

19. The system according to claim 14, further comprising a support mechanism having a recess configured to receive a proximal tail portion of the closure mechanism.

20. The system according to claim 14, wherein the delivery control mechanism effects coordinated axial rotation between a first end portion of the delivery mechanism and a second end portion of the delivery mechanism.

* * * * *